US010561726B2

(12) United States Patent
Swiss et al.

(10) Patent No.: US 10,561,726 B2
(45) Date of Patent: Feb. 18, 2020

(54) METHODS OF TREATING CANCER USING COMPOSITIONS OF ANTIBODIES AND CARRIER PROTEINS WITH ANTIBODY PRETREATMENT

(71) Applicants: Vavotar Life Sciences LLC, Cumming, GA (US); Mayo Foundation for Medical Education and Research, Rochester, MN (US)

(72) Inventors: Gerald F. Swiss, Rancho Santa Fe, CA (US); Svetomir N. Markovic, Rochester, MN (US); Wendy K. Nevala, Rochester, MN (US)

(73) Assignees: Vavotar Life Sciences LLC, Cumming, GA (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/092,403

(22) Filed: Apr. 6, 2016

(65) Prior Publication Data

US 2017/0095574 A1    Apr. 6, 2017

Related U.S. Application Data

(63) Continuation-in-part of application No. PCT/US2015/054295, filed on Oct. 6, 2015.

(60) Provisional application No. 62/252,377, filed on Nov. 6, 2015, provisional application No. 62/247,470, filed on Oct. 28, 2015.

(51) Int. Cl.
| | |
|---|---|
| *C07K 16/22* | (2006.01) |
| *A61K 39/395* | (2006.01) |
| *A61K 9/51* | (2006.01) |
| *A61K 47/46* | (2006.01) |
| *A61K 31/337* | (2006.01) |
| *C07K 16/30* | (2006.01) |
| *A61K 47/64* | (2017.01) |
| *A61K 47/69* | (2017.01) |
| *A61K 47/68* | (2017.01) |
| *A61K 39/00* | (2006.01) |

(52) U.S. Cl.
CPC ........ *A61K 39/3955* (2013.01); *A61K 31/337* (2013.01); *A61K 47/643* (2017.08); *A61K 47/6803* (2017.08); *A61K 47/6845* (2017.08); *A61K 47/6929* (2017.08); *C07K 16/22* (2013.01); *C07K 16/30* (2013.01); *A61K 2039/505* (2013.01); *A61K 2039/545* (2013.01); *A61K 2300/00* (2013.01); *C07K 2317/24* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | |
|---|---|---|
| 4,350,687 A | 9/1982 | Lipton et al. |
| 5,026,772 A | 6/1991 | Kobayashi et al. |
| 5,116,944 A | 5/1992 | Sivam et al. |
| 5,216,130 A | 6/1993 | Line et al. |
| 5,252,713 A | 10/1993 | Morgan, Jr. et al. |
| 5,260,308 A | 11/1993 | Poduslo et al. |
| 5,728,541 A | 3/1998 | Kornblith |
| 5,736,137 A | 4/1998 | Anderson et al. |
| 6,054,297 A | 4/2000 | Carter et al. |
| 6,147,060 A | 11/2000 | Zasloff et al. |
| 6,416,967 B2 | 7/2002 | Kornblith |
| 6,537,579 B1 | 3/2003 | Desai et al. |
| 6,933,129 B1 | 8/2005 | Kornblith |
| 7,041,301 B1 | 5/2006 | Markovic |
| 7,112,409 B2 | 9/2006 | Blumenthal et al. |
| 7,678,552 B2 | 3/2010 | Kornblith |
| 7,731,950 B2 | 6/2010 | Noessner et al. |
| 7,758,891 B2 | 7/2010 | Desai et al. |
| 7,820,788 B2 | 10/2010 | Desai et al. |
| 7,906,121 B2 | 3/2011 | Chang et al. |
| 7,923,536 B2 | 4/2011 | Desai et al. |
| 8,034,375 B2 | 10/2011 | Desai et al. |
| 8,119,129 B2 | 2/2012 | Jure-Kunkel et al. |
| 8,138,229 B2 | 3/2012 | Desai et al. |
| 8,268,348 B2 | 9/2012 | Desai et al. |
| 8,314,156 B2 | 11/2012 | Desai et al. |
| 8,344,177 B2 | 1/2013 | Neri et al. |
| 8,735,394 B2 * | 5/2014 | Desai .................. A61K 9/0019 514/252.01 |
| 8,853,260 B2 | 10/2014 | Desai et al. |
| 9,101,543 B2 | 8/2015 | Desai et al. |
| 9,387,244 B2 | 7/2016 | Markovic |

(Continued)

FOREIGN PATENT DOCUMENTS

| | | |
|---|---|---|
| EP | 1 913 947 A1 | 4/2008 |
| EP | 1 913 947 A1 | 4/2008 |

(Continued)

OTHER PUBLICATIONS

Rudikoff et al., Proc Natl Acad Sci USA 1982 vol. 79 pp. 1979-1983.*
Colman et al., Research in Immunology (145(1):33-36, 1994.*
Yu et al., Investigative Ophthalmology & Visual Science 49(2): 522-527, Feb. 2008.*
Stancovski et al., PNAS, 88: 8691-8695, 1991.*
Golay et al., Archives of Biochemistry and Biophysics 526: 146-153, 2012.*
Volk et al., Neoplasia 10(6): 613-623, Jun. 2008.*
Jain et al., Nature Medicine 7(9): 987-989.*

(Continued)

*Primary Examiner* — Phuong Huynh
(74) *Attorney, Agent, or Firm* — Myers Bigel, P.A.

(57) ABSTRACT

Described herein are methods, formulations and kits for treating a patient with cancer with anti-VEGF antibodies and albumin-bound chemotherapeutic/anti-VEGF antibody nanoparticle complexes.

11 Claims, 14 Drawing Sheets

(56) References Cited

U.S. PATENT DOCUMENTS

| | | |
|---|---|---|
| 9,427,477 B2 | 8/2016 | Markovic et al. |
| 9,446,148 B2 | 9/2016 | Markovic et al. |
| 9,466,148 B2 | 10/2016 | Gay et al. |
| 9,533,058 B2 | 1/2017 | Markovic et al. |
| 9,555,128 B2 | 1/2017 | Markovic et al. |
| 9,556,350 B2 | 2/2017 | Markovic et al. |
| 9,566,350 B2 | 2/2017 | Markovic et al. |
| 9,757,453 B2 | 9/2017 | Markovic et al. |
| 2002/0111362 A1 | 8/2002 | Rubinfeld |
| 2004/0005318 A1 | 1/2004 | Davis et al. |
| 2004/0077601 A1 | 4/2004 | Adams et al. |
| 2005/0032699 A1 | 2/2005 | Holash et al. |
| 2006/0165652 A1 | 7/2006 | Dudley et al. |
| 2007/0020232 A1 | 1/2007 | Rossignol et al. |
| 2007/0166388 A1 | 7/2007 | Desai et al. |
| 2009/0004118 A1 | 1/2009 | Nie et al. |
| 2010/0047234 A1 | 2/2010 | Markovic |
| 2010/0092489 A1 | 4/2010 | Van De Winkel et al. |
| 2010/0112077 A1* | 5/2010 | Desai ............... A61K 9/0019 424/499 |
| 2010/0172835 A1 | 7/2010 | Ruoslahti et al. |
| 2010/0260679 A1 | 10/2010 | Shachar et al. |
| 2010/0311679 A1 | 12/2010 | Olson et al. |
| 2011/0014117 A1 | 1/2011 | Wang et al. |
| 2011/0076273 A1 | 3/2011 | Adler et al. |
| 2011/0097340 A1 | 4/2011 | Ramachandra et al. |
| 2011/0104143 A1 | 5/2011 | Buchsbaum et al. |
| 2011/0150902 A1 | 6/2011 | Markovic |
| 2011/0262525 A1 | 10/2011 | Wang et al. |
| 2012/0263739 A1 | 10/2012 | Langer et al. |
| 2012/0315273 A1 | 12/2012 | Markovic |
| 2013/0028895 A1 | 1/2013 | Wulf |
| 2013/0071403 A1 | 3/2013 | Rolland et al. |
| 2013/0149238 A1 | 6/2013 | Kavlie et al. |
| 2013/0164816 A1 | 6/2013 | Chang et al. |
| 2014/0056909 A1 | 2/2014 | Markovic |
| 2014/0155344 A1 | 6/2014 | Desai et al. |
| 2014/0161819 A1 | 6/2014 | Hann et al. |
| 2014/0178486 A1 | 6/2014 | Markovic et al. |
| 2014/0302017 A1 | 10/2014 | Markovic |
| 2014/0314774 A1 | 10/2014 | Zhou et al. |
| 2015/0050356 A1 | 2/2015 | Desai et al. |
| 2015/0246122 A1 | 9/2015 | Markovic et al. |
| 2016/0095942 A1 | 4/2016 | Markovic et al. |
| 2016/0184229 A1 | 6/2016 | Markovic et al. |
| 2016/0184452 A1 | 6/2016 | Markovic et al. |
| 2016/0184453 A1 | 6/2016 | Markovic et al. |
| 2016/0235860 A1 | 8/2016 | Markovic et al. |
| 2016/0250351 A1 | 9/2016 | Markovic et al. |
| 2016/0256431 A1 | 9/2016 | Markovic et al. |
| 2016/0263241 A1 | 9/2016 | Markovic et al. |
| 2016/0310610 A1 | 10/2016 | Markovic et al. |
| 2016/0324964 A1 | 11/2016 | Markovic et al. |
| 2016/0338961 A1 | 11/2016 | Markovic et al. |
| 2016/0339118 A1 | 11/2016 | Markovic et al. |
| 2017/0021023 A1 | 1/2017 | Dikstein |
| 2017/0021032 A1 | 1/2017 | Markovic et al. |
| 2017/0021034 A1 | 1/2017 | Markovic et al. |
| 2017/0071897 A1 | 3/2017 | Markovic et al. |
| 2017/0095574 A1 | 4/2017 | Swiss et al. |
| 2017/0100492 A1 | 4/2017 | Markovic et al. |
| 2017/0106087 A1 | 4/2017 | Markovic et al. |
| 2017/0128408 A1 | 5/2017 | Markovic et al. |
| 2017/0128583 A1 | 5/2017 | Markovic et al. |
| 2017/0128584 A1 | 5/2017 | Markovic et al. |
| 2017/0128585 A1 | 5/2017 | Markovic et al. |
| 2017/0128586 A1 | 5/2017 | Markovic et al. |
| 2017/0128587 A1 | 5/2017 | Markovic et al. |
| 2017/0128588 A1 | 5/2017 | Markovic et al. |
| 2017/0182174 A1 | 6/2017 | Markovic et al. |
| 2017/0182175 A1 | 6/2017 | Markovic et al. |
| 2017/0182180 A1 | 6/2017 | Markovic et al. |
| 2017/0182183 A1 | 6/2017 | Markovic et al. |
| 2017/0182184 A1 | 6/2017 | Markovic et al. |
| 2017/0182185 A1 | 6/2017 | Markovic et al. |
| 2017/0182186 A1 | 6/2017 | Markovic et al. |
| 2017/0182187 A1 | 6/2017 | Markovic et al. |
| 2017/0196831 A1 | 7/2017 | Markovic et al. |
| 2017/0196832 A1 | 7/2017 | Markovic et al. |
| 2017/0196833 A1 | 7/2017 | Markovic et al. |
| 2017/0216453 A1 | 8/2017 | Markovic et al. |
| 2017/0232102 A1 | 8/2017 | Markovic et al. |
| 2017/0291952 A1 | 10/2017 | Markovic et al. |

FOREIGN PATENT DOCUMENTS

| | | |
|---|---|---|
| JP | S60146833 | 8/1985 |
| JP | S6178731 | 4/1986 |
| JP | H04504253 | 7/1992 |
| JP | 2001-072589 | 3/2001 |
| JP | 2001-72589 A | 3/2001 |
| KR | 10-2009-0078330 | 7/2009 |
| RU | 2011133819 | 2/2013 |
| WO | WO-89/10398 A1 | 11/1989 |
| WO | WO 89/10398 A1 | 11/1989 |
| WO | WO-97/49390 | 12/1997 |
| WO | WO-99/00113 A1 | 1/1999 |
| WO | WO 99/00113 A1 | 1/1999 |
| WO | WO-99/51248 A1 | 10/1999 |
| WO | WO 99/51248 A1 | 10/1999 |
| WO | WO-2004/096224 A2 | 11/2004 |
| WO | WO-2006/089290 A1 | 8/2006 |
| WO | WO2006/089290 A1 | 8/2006 |
| WO | WO2007/027819 A2 | 3/2007 |
| WO | WO2007/027941 A2 | 3/2007 |
| WO | 2008/047272 | 4/2008 |
| WO | 2008/057561 | 5/2008 |
| WO | WO 2008/057562 A1 | 5/2008 |
| WO | WO-2008/057562 A1 | 5/2008 |
| WO | WO 2008/112987 A1 | 9/2008 |
| WO | WO-2008/112987 A1 | 9/2008 |
| WO | WO 2009/043159 A1 | 4/2009 |
| WO | WO-2009/043159 A1 | 4/2009 |
| WO | WO 2009/055343 A2 | 4/2009 |
| WO | WO-2009/055343 A2 | 4/2009 |
| WO | WO 2010/003057 A2 | 1/2010 |
| WO | WO-2010/003057 A2 | 1/2010 |
| WO | WO-2010/017216 A2 | 2/2010 |
| WO | WO 2010/017216 A2 | 2/2010 |
| WO | WO2010/0118365 A1 | 10/2010 |
| WO | WO-2010/124009 | 10/2010 |
| WO | WO-2012/048223 A1 | 4/2012 |
| WO | WO 2012/048223 A1 | 4/2012 |
| WO | WO-2012/088388 A2 | 6/2012 |
| WO | WO 2012/154861 A2 | 11/2012 |
| WO | WO-2012/154861 A2 | 11/2012 |
| WO | WO2012154861 * | 11/2012 |
| WO | WO-2014/009774 | 1/2014 |
| WO | 2014/037422 | 3/2014 |
| WO | WO-2004/022097 A1 | 3/2014 |
| WO | WO-2014/055415 A1 | 4/2014 |
| WO | 2014/105644 | 7/2014 |
| WO | WO-2014/123612 | 8/2014 |
| WO | WO 2004/096224 A2 | 11/2014 |
| WO | WO-2015/048520 | 4/2015 |
| WO | WO-2015/191969 A1 | 12/2015 |
| WO | WO-2015/195476 A1 | 12/2015 |
| WO | WO 2016/057554 A1 | 4/2016 |
| WO | WO-2016/057554 A1 | 4/2016 |
| WO | WO-2016/059220 A1 | 4/2016 |
| WO | WO-2016/089873 | 6/2016 |
| WO | 2017/031368 | 2/2017 |
| WO | 2017/062063 | 4/2017 |
| WO | 2017/120501 | 7/2017 |
| WO | WO-2017/139698 A1 | 8/2017 |
| WO | 2017/165439 | 9/2017 |
| WO | 2017/165440 | 9/2017 |
| WO | 2017/176265 | 10/2017 |
| WO | 2018/027205 | 2/2018 |
| WO | 2018/045238 | 3/2018 |
| WO | 2018/045239 | 3/2018 |
| WO | 2018/048815 | 3/2018 |

(56) References Cited

FOREIGN PATENT DOCUMENTS

| WO | 2018/048816 | 3/2018 |
|---|---|---|
| WO | 2018/048958 | 3/2018 |

OTHER PUBLICATIONS

Yuan et al., Pro Natl. Acad. USA 93: 14765-14770, Dec. 1996.*
Jain et al., Jain 2 hereafter, Science 307: 58-62, Jan. 2005.*
Lloyd et al., Protein Engineering, Design & Selection 22:159-168 (Year: 2009).*
Edwards et al., J Mol Biol. 334(1): 103-118 (Year: 2003).*
International Search Report (PCT/ISA/210) issued in PCT Application No. PCT/US2016/026267 dated Jul. 12, 2016 (three (3) pages).
Written Opinion (PCT/ISA/237) issued in PCT Application No. PCT/US2016/026267 dated Jul. 12, 2016 (six (6) pages).
Kellen L. Meadows et al., "Anti-VEGF Therapies in the Clinic", Cold Spring Harbor Perspectives in Medicine, Oct. 1, 2012, vol. 2, pp. 1-27.
Priti S. Hegde et al., "Predictive Impact of Circulating Vascular Endothelial Growth Factor in Four Phase III Trials Evaluating Bevacizumab", Clinical Cancer Research, Feb. 15, 2013, vol. 19 (ten (10) pages).
Fausto Petrelli et al., "Targeted delivery for breast cancert therapy: the history of nanoparticle-albumin-bound paclitaxel", Expert Opinion on Pharmacotherapy, Jun. 1, 2010, vol. 11 (twenty-one (21) pages).
Abraxis Bioscience, Inc., "Abraxane: For the adjuvant treatment of node-positive breast cancer administered sequentially to standard doxorubicin-containing combination chemotherapy," Oncologic Drugs Advisory Committee Meeting (available to public Aug. 4, 2006).
Adams S, et al, "(P2-11-01) Safety and clinical activity of atezolizumab (anti-PDL1) in combination with nab-paclitaxel in patients with metastatictriple-negative breast cancer", 2015, 1 page.
Alessandra Fabi et al, "Prospective study on nanoparticle albumin-bound paclitaael in advanced breast cancer: clinical results and biological observations in taxane-pretreated patients", Drug Design, Development and Therapy vol. 9, Nov. 1, 2015, 7 pages.
Anonymous: "A Phase III, Multicenter, Randomized Placebo-Controlled Study of Atezolizumab (Anti-PD-L1 Antibody) in Combination with Nab Paclitaxel Compared with Placebo with Nab Paclitaxel for Patients with Previously Untreated Metastatic Triple Negative Breast Cancer", ClinicalTrials.gov, Apr. 21, 2015, 1 page.
Anonymous: "Atezolizumba Plus Abraxane Promising New Treatment for Triple-Negative Breast Cancer", UNM Comprehensive Cancer Center, Jan. 7, 2016, pp. 1-2.
Armitage, J.O. & Weisenburger, D.D. New approach to classifying non-Hodgkin's lymphomas: clinical features of the major histologic subtypes. Non-Hodgkin's Lymphoma Classification Project. J Clin Oncol 16, 2780-2795 (1998).
Desai (et al.), "Enhanced antitumor activity and safety of albumin-bound nab-docetaxel versus polysorbate 80-based docetaxel", Europeean Journal of Cancer. Supplement; 18th Symposium on Molecular Targets and Cancer Theraputics, vol. 4, No. 12, p. 49 (Nov. 2006).
Edison, "MorphoSys," 16 pages (Aug. 8, 2013).
Emens L et al, (OT1-01-06) A phase III randomized trial of atezolizumab in combination with nab-paclitaxel as first line therapy for patients with metastatic triple-negative breast cancer (mTNBC), 2015, 2 pages.
Erika Hamilton et al, "Nab-Paclitaxel/Bevacizumba/Carboplatin Chemotherapy in First-Line Triple Negative Metastatic Breast Cancer", Clinical Breast Cancer, vol. 13, No. 6, Dec. 1, 2013, 6 pages.
Flores (et al.), "Novel oral taxane therapies: recent Phase I results," Clinical Investigation, vol. 3, No. 4, p. 333-341 (Apr. 1, 2013).
Giorgio Mustacchi et al, "The role of taxanes in triple-negative breast cancer: literature review", Drug Design, Development and Therapy, vol. 9, Aug. 5, 2015, 16 pages.

Hassan (et al.), "Comparison of Different Crosslinking Methods for Preparation of Docetaxel-loaded Albumin Nanoparticles," Iranian Journal of Pharmaceutical Research, vol. 14, No. 2, p. 385-394 (Apr. 2015).
Hegde et al., "Predictive impact of circulating vascular endothelial growth factor in four phase III trials evaluating bevacizumab," Clinical Cancer Research, vol. 19, pp. 929-937 (Feb. 15, 2013).
International Search Report and Written Opinion, PCT/US2017/050137, dated Nov. 27, 2017, 17 pages.
International Search Report and Written Opinion, PCT/US2016/026267, Mayo Foundation for Medical Education and Research, 9 pages (dated Jul. 12, 2016).
International Search Report and Written Opinion, PCT/US2016/026270, Mayo Foundation for Medical Education and Research, 10 pages (dated Jan. 26, 2017).
International Search Report and Written Opinion, PCT/US2017/023442, Mayo Foundation for Medical Education and Research, 8 pages (dated Jun. 16, 2017).
International Search Report and Written Opinion, PCT/US2017/023443, Mayo Foundation for Medical Education and Research, 10 pages (dated Jul. 11, 2017).
International Search Report and Written Opinion, PCT/US2017/045643, dated Oct. 25, 2017, 16 pages.
International Search Report and Written Opinion, PCT/US2017/049745, Mayo Foundation for Medical Education and Research, 13 pages (dated Dec. 15, 2017).
International Search Report and Written Opinion, PCT/US2017/049746, dated Nov. 27, 2017, 15 pages.
International Search Report and Written Opinion, PCT/US2017/050134, dated Nov. 16, 2017, 17 pages.
International Search Report and Written Opinion, PCT/US2017/050355, Mayo Foundation for Medical Education and Research, 19 pages (dated Jan. 30, 2018).
Jaime et al., "Paclitaxel antibody conjugates and trehalose for preserving the immunological activity after freeze-drying," Curr. Med. Chem., 11(4), pp. 439-446, Abstract Only (Feb. 2004).
Jin (et al.), "Docetaxel-loaded PEG-albumin nanoparticles with improved antitumor efficiency against non-small cell lung cancer," Oncology Reports, vol. 36, No. 2, p. 871-876 (Aug. 8, 2016).
Jin et al., "Paclitaxel-loaded nanoparticles decorated with anti-CD133 antibody: a targeted therapy for liver cancer stem cells," J. Nanopart. Res., 16:2157, 15 pages (Dec. 4, 2013).
Kazuhiro Nishida et al, English Translation of "Clinical Trails of New Drugs Cytotoxic Effect against Multiple Myeloma with High Expression of a CD38 Antigen and a Human CD38 Monoclonal Antibody Daratumumab:CD38 Antigen", history of Medicine, Sep. 29, 2012, vol. 242, No. 13, pp. 1176-1181.
Korean Office Action, App. No. 10-2016-7035909, 7 pages (Dec. 19, 2017).
Lee, A, et al., "The co-delivery of paclitaxel and Herceptin using cationic micellar nanoparticles", Biomaterials Elsevier Science Publishers BV., Barking, GB, vol. 30, No. 5, Feb. 1, 2009, pp. 919-927.
Lisa D Volk-Draper et al, "Novel Model for Basaloid Triple-negative Breast Cancer: Behavior In Vivo and Response to Therapy", vol. 14, No. 10, Oct. 1, 2012, 18 pages.
Meadows et al., "Anti-VEGF therapies in the clinic," Cold Spring Harbor Perspectives in Medicine, vol. 2. pp. 1-27 (Oct. 1, 2012).
Na (et al.), "Cabazitaxel-loaded human serum albumin nanoparticles as a therapeutic agent against prostate cancer," International Journal of Nanomedicine, vol. 11, p. 3451-3459 (Jul. 26, 2016).
Nahleh et al, "Swog S0800 (NCI CDR0000636131): addition of bevacizumba to neoadjuvant nab-paclitaxel with dose-dense doxorubicin and cyclophosphamide improves pathologic complete response (pCR) rates in inflammatory or locally advanced breast cancer", Breast Cancer Research and Treatment, vol. 158, No. 3 Jul. 8, 2016, 12 pages.
Parker, Edward et al., "Targeting CLL Cells Using Rituximab-Conjugated Surface Enhanced Raman Scattering (SERS) Gold Nanoparticles", Blood, American Society of Hematology, US, vol. 116, No. 21, Nov. 1, 2010, p. 1109.
Petrelli et al., "Targeted delivery for breast cancer therapy: the history of nanoparticle-albumin-bound paclitaxel," Expert Opinion on Pharmacotherapy, vol. 11, pp. 1413-1432 (Jun. 1, 2010).

(56) References Cited

OTHER PUBLICATIONS

Samaranayake (et al.), "Modified Taxols.5.1 Reaction of Taxol with electrophilic Reagents and Preparation of a Rearranged Taxol Derivative with Tubulin Assembly Activity," The Journal of Organic Chemistry, vol. 56, p. 5114-5119 (1991).
Silas Inman, "Atezolizumab/Nab-Paclitaxel Combo Shows High Response Rates in TNBC", OneLive, Dec. 10, 2015, 4 pages.
Sylvia Adams et al, "Phase Ib trial of atezolizumab in combination with nab-paclitaxel in patients with metastatic triple-negative breast cancer (mTNBC)" Journal of Clinical Oncology col. 34, No. 15, May 1, 2016, 4 pages.
Vishnu, P. et al., Safety and efficacy of nab-paclitaxel in the treatment of patients with breast cancer, Breast Cancer: Basic and Clinical Research, vol. 5, pp. 53-65 (2011).
Wendy K. Nevala et al, "Abstract B77: Targets nano-immune conjugates to melanoma: Preclinical testing of bevacizumab targeted nab-paclitaxel", Cancer Immunology Research, vol. 3, Oct. 1, 2015, 3 pages.
Wendy K. Nevala et al, "Antibody—targeted paclitaxel loaded nanoparticles for the treatment of CD20 B-cell lymphoma", Scientific Reports, vol. 7, Apr. 5, 2017, 9 pages.
Wendy K. Nevala et al, "Antibody-Targeted Chemotherapy for the Treatment of Melanoma", Cancer Research, vol. 76, No. 13, Jul. 1, 2016, pp. 3954-3964.
Wendy K. Nevala et al, "Targeted nano-immune conjugates to melanoma: Preclinical testing of bevacizumab targeted nab-paclitaxel", Proceedings of the AACR Special Conference: Tumor Immunology and Immunotherapy: A New Chapter, Dec. 1, 2014, 2 pages.
Yashito Terui, English Translation of Molecular-Targeted Therapy for Cancer: Progresses and Challenges, "Daratumumab, Antibody Drug against Myeloma", Pharma Med., Nov. 10, 2013, vol. 31, No. 11, p. 27-30.
"A Study of Bevacizumab With Carboplatin and Paclitaxel Chemotherapy for the First-Line Treatment of Patients With Metastatic Melanoma (BEAM)," ClinicalTrials.gov [online]. Retrieved from the Internet: <URL: https://clinicaltrials.gov/archive/NCT00434252/200703 12>, dated Mar. 12, 2007, 3 pages.
"Concurrent Infusions", J Oncol Pract., 4(4): 171, Jul. 2008.
AACR Presentation, "Targeted nano-immune conjugates to melanoma: Pre-clinical testing of bevacizumab targeted nab- paclitaxel," Mayo Clinic, 2014.
Abraxane® for Injectable Suspension (paclitaxel protein-bound particles for injectable suspension) (albumin-bound), [drug label], 22 pages, Sep. 2009.
Agarwal et al., "Flow Cytometric analysis of Th1 and Th2 cytokines in PBMCs as a parameter of immunological dysfunction in patients of Superficial Transitional cell carcinoma of bladder", Cancer Immunol. Immunother., 2006, 55(6):734-743.
Agarwala et al., "Randomized phase III study of paclitaxel plus carboplatin with or without sorafenib as second-line treatment in patients with advanced melanoma", J. Clin. Oncol., 2007, 25(185):8510 (Abstract).
Allen, TM, "Ligand-targeted therapeutics in anticancer therapy, Cancer", Oct. 2002, 2(10), pp. 750-763.
Alley et al., "Contribution of Linker Stability to the Activities of Anticancer Immunoconjugates", Bioconjugate Chem., 2008, 19(3), pp. 759-765.
Anonymous, "A Phase II , multicenter, randomized, double-blind placebo-controlled trial evaluating the efficacy and safety of bevacizumab in combination with carboplatin and paclitaxel chemotherapy for the first-line treatment of patients with metastatic melanoma", U.S. National Institutes of Health, 2007, 3 pages.
Anonymous, "Phase II trial of carboplatin, weekly paclitaxel and biweekly bevacizumab in patients with unresectable stage IV melanoma", U.S. National Institutes of Health , 2007, 4 pages.
Arakawa et al., "Protein-Solvent Interactions in Pharmaceutical Formulations", Pharm. Res., Mar. 1991, vol. 8, Issue 3, pp. 285-291.
Asadullah et al., "Interleukin-10 therapy—review of a new approach", Pharmarcol Rev., 2003, 55(2):241-269.
Atkins et al., "High-dose recombinant interleukin-2 therapy in patients with metastatic melanoma: long-term survival update", Cancer J Sci Am., 2000, Suppl 6:S11-14.
Atkins, Michael, "Interleukin-2: clinical applications", Semin Oncol., 2002, 29(3 Suppl 7):12-27.
Avastin® Bevacizumab, Roche, [drug label], 24 pages, Sep. 2008.
Bairagi et al., Albumin: A Versatile Drug Carrier, Austin Therapeutics, (Nov. 17, 2015) vol. 2, No. 2, p. 1021 (pp. 1-6), especially abstract, p. 2, Table 2, p. 2 col. 2 para. 2.
Balch et al., "The new melanoma staging system", Semin Cutan Med Surg., 2003, 22(1):42-54.
Balch et al., "Update on the melanoma staging system: The importance of sentinel node staging and primary tumor mitotic rate", Journal of Surgical Oncology, Aug. 19, 2011, vol. 104, Issue 4, pp. 379-385.
Bauer, K., et al., "Rituximab, ofatumumab, and other monoclonal anti-CD20 antibodies for chronic lymphocytic leukaemia (Review)," Cochrane Database of Systematic Reviews, Issue 11, 125 pages (copyright 2012).
Baumgartner et al., "Melanoma induces immunosuppression by up-regulating FOXP3(+) regulatory T cells", J Surg Res., 2007, 141(1): 72-77.
Belani et al., "Multicenter, randomized trial for stage IIIB or IV non-small-cell lung cancer using weekly paclitaxel and carboplatin followed by maintenance weekly paclitaxel or observation", J. Clin. Oncol., 2003, 21:2933-2939.
Bird et al., "Single-chain antigen-binding proteins", Science, Oct. 1988, 242(4877), pp. 423-426.
Boasberg et al., "Phase II trial of nab-paclitaxel and bevacizumab as first-line therapy in patients with unresectable melanoma", Journal of Clinical Oncology, May 20, 2011, vol. 29, No. 15 Supp, 8543.
Boasberg et al., Nab-paclitaxel and bevacizumab as first-line therapy in patients with unresectable stage III and IV melanoma, J Clin Oncol., 27:15s, 2009 (suppl; abstr 9061), 2009 ASCO Annual Meeting, Retrieved from the Internet: <URL: http://meetinglibrary.asco.org/print/584876>, 2 pages, 2009.
Bolstad et al., "A comparison of normalization methods for high density oligonucleotide array data based on variance and bias", Bioinformatics, 2003, 19:185-193.
Cao et al., "Response of resistant melanoma to a combination of weekly paclitaxel and bevacizumab", Clin Transl Oncol, 2007, 9:119-120.
Carson et al., "A phase 2 trial of a recombinant humanized monoclonal anti-vascular endothelial growth factor (VEGF) antibody in patients with malignant melanoma", Proceedings of the ASCO vol. 22, No. 2873, General Poster Session, Thirty-Ninth Annual Meeting of the American Society of Clinical Oncology, May 31-Jun. 3, 2003, Chicago, IL, 2 pages.
Celis, "Overlapping human leukocyte antigen class I/II binding peptide vaccine for the treatment of patients with stage IV melanoma: evidence of systemic immune dysfunction", Cancer, 2007, 110(1):203-214.
Chapman et al., "Improved Survival with Vemurafenib in Melanoma with BRAF V600E Mutation", The New England Journal of Medicine, Jun. 30, 2011, vol. 364, Issue 26, pp. 2507-2516.
Chisholm et al., "Response to influenza immunization during treatment for cancer", Arch Dis Child, 2001, 84(6):496-500.
Chong et al., "Combining cancer vaccines with chemotherapy", Expert Opin Pharmacother., 2006, 6(16):2813-2820.
Cleland et al., "The Development of Stable Protein Formulations: A close look at protein aggregation, deamidation, and oxidation", Therapeutic Drug Carrier Systems, 1993, 10(4), pp. 307-377.
Davis, "Affinity separation of antibody-toxin conjugate from albumin-stabilized formulation", Am Biotechnol Lab., 12(4):60-64, Mar. 1994.
Degrasse, J.A., "A Single-Stranded DNA Aptamer That Selectively Binds to *Staphylococcus aureus* Enterotoxin B", PLoS One, 2012, 7(3) e33410, pp. 1-7.
Deguchi et al., "Effect of Methotrexate-Monoclonal Anti-Prostatic Acid Phosphatase Antibody Conjugate on Human Prostate Tumor", Cancer Research, Aug. 1986, 46, pp. 3751-3755.
Demirkesen et al., "The correlation of angiogenesis with metastasis in primary cutaneous melanoma: a comparative analysis of microves-

(56) References Cited

OTHER PUBLICATIONS sel density, expression of vascular endothelial growth factor and basic fibroblastic growth factor", Pathology, 2006, 38:132-137.
Denardo et al., "Inflammation and breast cancer. Balancing immune response: crosstalk between adaptive and innate immune cells during breast cancer progression", Breast Cancer Res., 2007, 9(4):212.
Desai et. al., "Increased antitumor activity, intratumor paclitaxel concentrations, and endothelial cell transport of cremophor-free, albumin-bound paclitaxel, ABI-007, compared with cremophor-based paclitaxel", Clin Cancer Res., 2006, 12(4): 1317-24.
Deweers et al., "Daratumumab, a novel therapeutic human CD38 monoclonal antibody, induces killing of multiple myeloma and other hematological tumors", J. Immunol., 186(3): 1840-1848, Feb. 1, 2011.
Dudek et al., "Autologous large multivalent immunogen vaccine in patients with metastatic melanoma and renal cell carcinoma", Am. J. Clin. Oncol., Apr. 1, 2008, 31(2):173-181.
Elbayoumi et al., "Tumor-Targeted Nanomedicines: Enhanced Antitumor Efficacy in vivo of Doxorubicin-Loaded, Long-Circulating Liposomes Modified with Cancer-Specific Monoclonal Antibody", Clin Cancer Res., 2009, 15(6):1973-1980.
Ellyard et al., "Th2-mediated anti-tumour immunity: friend or foe?", Tissue Antigens, 2007, 70(1):1-11.
Elsadek et al., "Impact of albumin on drug delivery—New applications on the horizon", J of Controlled Release, 2011, 1-25.
Ferrara et al., "The biology of VEGF and its receptors", Nat. Med., 2003, 9:669-676.
Flaherty et al., "Final Results of E2603: a double-blind, randomized phase III trial comparing carboplatin (C)/paclitaxel(P) with or without sorafenib(S) in metastatic melanoma", J. Clin Oncol., 2010, 28:15s (suppl: abstr 8511).
Folkman, J., "Angiogenesis in cancer, vascular, rheumatoid and other disease", Nat. Med., 1995, 1, 27-31.
Fricke et al., "Vascular endothelial growth factor-trap overcomes defects in dendritic cell differentiation but does not improve antigen-specific immune responses", Clin. Cancer Res., 2007, 13:4840-4848.
Gabrilovich et al., "Production of vascular endothelial growth factor by human tumors inhibits the functional maturation of dendritic cells", Nat. Med., 1996, 2: 1096-1103.
Gao et al., "In vivo cancer targeting and imaging with semiconductor quantum dots", Nat Biotech, 2004, 22(8):969-976.
Gogas et al., "Chemotherapy for metastatic melanoma: time for a change?", Cancer, 2007, 109(3): 455-464.
Graells et al., "Overproduction of VEGF16s concomitantly expressed with its receptors promotes growth and survival of melanoma cells through MAPK and PI3K signaling", J. Invest. Dermatol., 2004, 123:1151-1161.
Gupta, I., et al., "Ofatumumab, the first human anti-CD20 monoclonal antibody for the treatment of B cell hematologic malignancies," Ann. N.Y. Acad. Sci., 1263, pp. 43-56 (Jul. 25, 2012).
Haley et al., "Nanoparticles for drug delivery in cancer treatment", Urol. Oncol.: Seminars and Original Invest., 2008, 26:57-64.
Hauschild et al., "Individualized therapy of disseminated cancer using malignant melanoma as a model", Cancer and Metastasis Reviews, 2006, 25(2): 253-256.
Hauschild et al., "Results of a Phase III, Randomized, Placebo-Controlled Study of Sorafenib in Combination with Carboplatin and Paclitaxel as Second-Line Treatment in Patients with Unresectable Stage III or Stage IV Melanoma", Journal of Clinical Oncology, Jun. 10, 2009, vol. 27, No. 17, pp. 2823-2830.
Hersh et al., "A Phase 2 Clinical Trial of nab-Paclitaxel in Previously Treated and Chemotherapy-Naïve Patients With Metastatic Melanoma", Cancer, Jan. 1, 2010, 116:155, pp. 155-163.
Hersh et al., "A randomized, controlled phase III trial of nab-Paclitaxel versus dacarbazine in chemotherapy-naïve patients with metastatic melanoma", Ann Oncol, 2015, epub Sep. 26, 2015.
Hersh et al., "Open-label, multicenter, phase II trial of ABI-007 in previously treated and previously untreated patients with metastatic malignant melanoma", J. Clin. Oncol., 2005, 23(16S):7558 (Abstract).

Hobbs et al., "Regulation of Transport pathways in tumor vessels: role of tumor type and microenvironment", Proc Natl Acad Sci USA, Apr. 1998, 95, pp. 4607-4612.
Hodi et al., "Improved survival with ipilimumab in patients with metastatic melanoma", The New England Journal of Medicine, Aug. 19, 2010, vol. 363, No. 8, pp. 711-723.
Hodi et al., "Phase II study of paclitaxel and carboplatin for malignant melanoma", Am. J. Clin. Oncol., 2002, 25:283-286.
Huncharek et al., "Single-agent DTIC versus combination chemotherapy with or without immunotherapy in metastatic melanoma: a meta-analysis of 3273 patients from 20 randomized trials", Melanoma Research, 11:75-81 (2001).
Hunkapiller et al., "Immunology: The growing immunoglobulin gene superfamily", Nature, Sep. 1986, 323, pp. 15-16.
Huston et al., "Protein engineering of antibody binding sites: Recovery of specific activity in an anti-digoxin single-chain Fv analogue produced in *Escherichia coli*", Proc. Natl. Acad. Sci. USA, Aug. 1988, vol. 85, pp. 5879-5883.
Ibrahim et al., "Phase I and Pharmacokinetic Study of ABI-007, a Cremophor-free, Protein-stabilized, Nanoparticle Formulation of Paclitaxel", Clinical Cancer Research, May 2002, vol. 8, pp. 1038-1044.
Inagaki et al., "Clinical significance of serum Th1-, Th2- and regulatory T cells-associated cytokines in adult T-cell leukemia/lymphoma: High interleukin-5 and -10 levels are significant unfavorable prognostic factors", Int. J. Cancer, 2006, 118(12):3054-3061.
International Preliminary Report on Patentability for Application No. PCT/US2012/037137 dated Nov. 12, 2013, 5 pages.
International Preliminary Report on Patentability for Application No. PCT/US2008/057025, dated Sep. 15, 2009, 6 pages.
International Preliminary Report on Patentability for Application No. PCT/US2009/049511, dated Jan. 5, 2011, 6 pages.
International Preliminary Report on Patentability for Application No. PCT/US2013/062638, dated Apr. 16, 2015, 11 pages.
International Preliminary Report on Patentability, PCT/US2015/035505, Mayo Foundation for Medical Education and Research, 10 pages (dated Dec. 22, 2016).
International Preliminary Report on Patentability, PCT/US2015/035515, Mayo Foundation for Medical Education and Research, 18 pages (dated Dec. 29, 2016).
International Search Report and Written Opinion for Application No. PCT/US15/35505 dated Nov. 24, 2015. 17 pages.
International Search Report and Written Opinion for Application No. PCT/US15/35515 dated Sep. 21, 2015. 23 pages.
International Search Report and Written Opinion for Application No. PCT/US16/47641 dated Oct. 31, 2016, 11 pages.
International Search Report and Written Opinion for Application No. PCT/US17/17553 dated Feb. 10, 2017, 13 pages.
International Search Report and Written Opinion for Application No. PCT/US2008/057025, dated Jul. 1, 2008, 11 pages.
International Search Report and Written Opinion for Application No. PCT/US2009/049511, dated Feb. 2, 2010, 8 pages.
International Search Report and Written Opinion for Application No. PCT/US2012/037137 dated Sep. 28, 2012, 5 pages.
International Search Report and Written Opinion for Application No. PCT/US2013/062638, dated Jan. 23, 2014, 19 pages.
International Search Report and Written Opinion for Application No. PCT/US2015/054295 dated Jan. 25, 2016, 15 pages.
Jain et al., "Delivering nanomedicine to solid tumors", Nature Reviews Clinical Oncology, Nov. 2010, 7, pp. 653-664.
Jazirehi et al., "Rituximab (anti-CD20) selectively modifies Bcl-xl and apoptosis protease activating factor-1 (Apaf-1) expression and sensitizes human non-Hodgkin's lymphoma B cell lines to paclitaxel-induced apoptosis," Mol. Cancer Ther., (2003), 2:1183-1193.
Jiang et al., "Regulation of Immune Responses by T Cells", N Engl J Med., 2006, 354(11): 1166-1176.
Julien et al, "Utilization of monoclonal antibody-targeted nanomaterials in the treatment of cancer", 2011, MAbs, 3:467-478.
Kamat et al., "Metronomic chemotherapy enhances the efficacy of antivascular therapy in ovarian cancer", Cancer Res., 2007, 67(1):281-288.

(56) References Cited

OTHER PUBLICATIONS

Kawai et al., "VEGF121 promotes lymphangiogenesis in the sentinel lymph nodes of non-small cell lung carcinoma patients", Lung Cancer, 2008, 59(1):41-47.

Kikuchi et al., "Vascular endothelial growth factor and dendritic cells in human squamous cell carcinoma of the oral cavity", Anticancer Res., 2006, 26(3A):1833-1848.

Kim et al., "A Dual Target-directed Agent against Interleukin-6 Receptor and Tumor Necrosis Factor a ameliorates experimental arthritis", Scientific Reports, 2016, pp. 1-12.

Kim et al., "Beam: A Randomized Phase II Study Evaluating the Activity of Bevacizumab in Combination with Carboplatin Plus Paclitaxel in Patients With Previously Untreated Advanced Melanoma", Journal of Clinical Oncology: official journal of the American Society of Clinical Oncology, Jan. 1, 2012, vol. 30, No. 1, pp. 34-41.

Kirkwood et al., "A pooled analysis of eastern cooperative oncology group and intergroup trials of adjuvant high-dose interferon for melanoma", Clin Cancer Res., 2004, 10(5):1670-1677.

Kondejewski et al., "Synthesis and characterization of carbohydrate-linked murine monoclonal antibody K20-human serum albumin conjugates", Bioconjug Chem., 5(6):602-611, Nov.-Dec. 1994.

Korman et al., "Tumor immunotherapy: preclinical and clinical activity of anti-CTLA4 antibodies", Curt Opin Invest Drugs, 2005, 6(6):582-591.

Kottschade et al., "A Phase II Trial of Nab-Paclitaxel (ABI-007) and Carboplatin in Patients with Unresectable Stage IV Melanoma", Cancer, Apr. 15, 2011, 117(8), pp. 1704-1710.

Kottschade et al., "A Randomized Phase 2 Study of Temozolomide and Bevacizumab or nab-Paclitaxel, Carboplatin, and Bevacizumab in Patients with Unresectable Stage IV Melanoma", Cancer, 2013, vol. 119, Issue 3, pp. 586-592.

Kratz et al., "Serum proteins as drug carriers of anticancer agents: a review", Drug Deliv., 5(4):281-299, 1998.

Kratz, "Albumin as a drug carrier: design of prodrugs, drug conjugates and nanoparticles", J Control Release, 132(3):171-183, Epub May 17, 2008.

Krishnan et al., "Programmed death-1 receptor and interleukin-10 in liver transplant recipients at high risk for late cytomegalovirus disease", Transpl Infect Dis., 12(4):363-70, print Aug. 2010, ePub Jan. 2010.

Kukowska-Latallo et al., Nanoparticle Targeting of Anticancer Drug Improves Therapeutic Response in Animal Model of Human Epithelial Cancer, Cancer Res, 2005, 65(12):5317-5324.

Kumar et al., Th1/Th2 cytokine imbalance in meningioma, anaplastic astrocytoma and glioblastoma multiforme patients, Oncol. Rep., 2006, 15(6):1513-1516.

Lanzavecchia et al., "The use of hybrid hybridomas to target human cytotoxic T lymphocytes", Eur. J. Immunol., 1987, 17, pp. 105-111.

Lau et al., Is inhibition of cancer angiogenesis and growth by paclitaxel schedule dependent?, Anti-Cancer Drugs, 2004, 15:871-875.

Lei et al., Comparing cellular uptake and cytotoxicity of targeted drug carriers in cancer cell lines with different drug resistance mechanisms, Nanomed: Nanotech, Biol, and Med., 2011, 7:324-332.

Lev et al., Dacarbazine causes transcriptional up-regulation of interleukin 8 and vascular endothelial growth factor in melanoma cells: a possible escape mechanism from chemotherapy, Mol. Cancer Ther., 2003, 2:753-763.

Lev et al., Exposure of melanoma cells to dacarbazine results in enhanced tumor growth and metastasis in vivo, J. Clin. Oncol., 2004, 22:2092-2100.

Lin, S.Y, "Salmon calcitonin: conformational changes and stabilizer effects", AIMS Biophysics, 2015, 2(4): 695-723.

Lundin et al., Phase 2 Study of Alemtuzumab (anti-CD52 Monoclonal Antibody)in Patients with Advanced Mycosis Fungoides/Sezary Syndrome, Blood. (Jun. 1, 2003) vol. 101, No. 11, pp. 4267-72, especially p. 4267 col. 1, para. 1, p. 4267 col. 2, para 2-p. 4268 col. 1, para. 1, p. 4271 col. 1, para. 3.

Marcoval et al., Angiogenesis and malignant melanoma. Angiogenesis is related to the development of vertical (tumorigenic) growth phase, J. Cutan. Pathol., 1997, 24:212-218.

Markovic et al., A phase II study of ABT-510 (thrombospondin-1 analog) for the treatment of metastatic melanoma, Am. J. Clin. Oncol., 2007, 30(3):303-309.

Markovic et al., A reproducible method for the enumeration of functional ( cytokine producing) versus non-functional peptide-specific cytotoxic T lymphocytes in human peripheral blood, Clin. Exo. Immunol., 2006, 145:438-447.

Markovic et al., Peptide vaccination of patients with metastatic melanoma: improved clinical outcome in patients demonstrating effective immunization, Am J Clin Oncol., 2006, 29(4):352-360.

Matejtschuk, P., "Lyophilization of Proteins", Methods in Molecular Biology, Cryopreservation and Freeze-Drying Protocols, Second Edition, Edited by: J. G. Day and G. N. Stacey © Humana Press Inc., Totowa, NJ, 2007, vol. 368, pp. 59-72.

Matsuda et al., Preoperative oral immune-enhancing nutritional supplementation corrects TH1/TH2 imbalance in patients undergoing elective surgery for colorectal cancer, Dis. Colon Rectum, 2006, 49(4):507-516.

Mayo Clinic: Paclitaxel Albumin-Stabilized Nanoparticle Formulation and Bevacizumab in Treating Patients With Stage IV Melanoma That Cannot Be Removed by Surgery—Full Text View ClinicalTrials.gov, Dec. 19, 2013, pp. 1-4, Retrieved from the Internet URL:https//clinicaltrials.gov/ct2/show/NCT02020707?term=targeted+nanoparticle+therapy+for+advanced+melanoma&rank=1 [retrieved on Jan. 6, 2016].

McElroy et al., Imaging of Primary and Metastatic Pancreatic Cancer Using a Fluorophore-Conjugated Anti-CA19-9 Antibody for Surgical Navigation, World J Surg., 2008, 32: 1057-1066.

Melcher, Recommendations for influenza and pneumococcal vaccinations in people receiving chemotherapy, Clin Oncol (R Coll Radiol), 2005, 17(1): 12-15.

Merchan et al., Increased endothelial uptake of paclitaxel as a potential mechanism for its antiangiogenic effects: potentiation by Cox-2 inhibition, Int. J. Cancer, 2005, 113, pp. 490-498.

Mezzaroba et al., "New potential therapeutic approach for the treatment of B-Cell malignancies using chlorambucil/Hydroxychloroquine-Loaded Anti-CD20 Nanoparticles", Sep. 2103, PLoS One vol. No. 8, Issue 9 pp. 1-10, e74216.

Middleton et al., Randomized phase III study of temozolomide versus dacarbazine in the treatment of patients with advanced metastatic malignant melanoma, J. Clin. Oncol., 2000, 18, pp. 158-166.

Miller et al. "Paclitaxel plus Bevacizumab versus Paclitaxel Alone for Metastatic Breast Cancer," N Engl. J Med., (2007) vol. 357:2666-2676.

Mimura et al., Vascular endothelial growth factor inhibits the function of human mature dendritic cells mediated by VEGF receptor-2, Cancer Immunol Immunother., 2007, 56(6). pp. 761-770.

Mirtsching et al., "A Phase II Study of Weekly Nanoparticle Albumin-Bound Paclitaxel With or Without Trastuzumab in Metastatic Breast Cancer", Clinical Breast Cancer, 2011, 11(2):121-128.

Mocellin et al., Cytokines and immune response in the tumor microenvironment, J Immunother., 2001, 24(5), pp. 392-407.

Motl, S., Bevacizumab in combination chemotherapy for colorectal and other cancers, Am. J. Health-Syst. Pharm 2005, 62:1021-1032.

Ng et al., Influence of formulation vehicle on metronomic taxane chemotherapy: albumin-bound versus cremophor EL-based paclitaxel, Clin. Cancer Res., 2006, 12, pp. 4331-4338.

Ng et al., Taxane-mediated antiangiogenesis in vitro: influence of formulation vehicles and binding proteins, Cancer Res., 2004, 64, pp. 821-824.

Nilvebrant et al., "The Albumin-Binding Domain as a Scaffold for Protein Engineering", Computational and Structural Biotechnology Journal, Mar. 2013, vol. 6, Issue 7, e201303099, http://dx.doi.org/10.5936/csbj.201303099.

Oku et al., Tumor growth modulation by sense and antisense vascular endothelial growth factor gene expression: effects on angiogenesis, vascular permeability, blood volume, blood flow,

(56) References Cited

OTHER PUBLICATIONS fluorodeoxyglucose uptake, and proliferation of human melanoma intracerebral xenografts, Cancer Res., 1998, 58, pp. 4185-4192.
Parikh et al., The vascular endothelial growth factor family and its receptors, Hematol. Oncol. Clin. N. Am., 2004, 18, pp. 951-971.
Park et al., Anti-HER2 Immunoliposomes: Enhanced Efficacy Attributable to Targeted Delivery, Clin. Cancer Res., 2002, 8, pp. 1172-1181.
Perez et al., "Phase 2 trial of carboplatin, weekly paclitaxel, and biweekly bevacizumab in patients with unresectable stage IV melanoma," A north central cancer treatment group study, Cancer, 2009, 115(1), pp. 119-127.
Phase II: A Study of Bevacizumab With Carboplatin and Paclitaxel Chemotherapy for the First-Line Treatment of Patients With Metastatic Melanoma (BEAM) Mar. 12, 2007, [retrieved Mar. 15, 2010]. Retrieved from the Internet: <URL:http://clinicaltrials.gov/archive/NCT00434252/2007 03 12>, 3 pages.
Pikal, M., Freeze-drying of proteins, Part II: Formulation selection, Biopharm, 1990, 9, pp. 26-30.
Polak et al., Mechanisms of local immunosuppression in cutaneous melanoma, Br J Cancer, 2007, 96(12), pp. 1879-1887.
Porrata et al., Early lymphocyte recovery predicts superior survival after autologous hematopoietic stem cell transplantation in multiple myeloma or non-Hodgkin lymphoma, Blood, 2001, 98(3), pp. 579-585.
Porrata et al., Timely reconstitution of immune competence affects clinical outcome following autologous stem cell transplantation, Clin Exp Med., 2004, 4(2):78-85.
Powell et al., Adoptive transfer of vaccine-induced peripheral blood mononuclear cells to patients with metastatic melanoma following lymphodepletion, J Immunol., 2006, 177(9), pp. 6527-6539.
Pries et al., Cytokines in head and neck cancer, Cytokine Growth Factor Rev., 2006, 17(3), pp. 141-146.
Ranieri et al., "Vascular endothelial growth factor (VEGF) as a target of bevacizumab in cancer: from the biology to the clinic", Curr. Med. Chem., 2006, 13, 1845-1857.
Rao et al., "Combination of paclitaxel and carboplatin as second-line therapy for patients with metastatic melanoma", Cancer, 2006, 106(2), 375-382.
Ribas et al., "Antitumor activity in melanoma and anti-self responses in a phase I trial with the anti-cytotoxic T lymphocyte-associated antigen 4 monoclonal antibody CP-675,206", J Clin Oncol., Dec. 10, 2005, 23(35), pp. 8968-8977.
Rosenberg et al., "Tumor progression can occur despite the induction of very high levels of self/tumor antigen-specific CD8+ T cells in patients with melanoma", J. Immunol., 2005, 175(9), pp. 6169-6176.
Roy et al., "Tumor associated release of interleukin-10 alters the prolactin receptor and down—regulates prolactin responsiveness of immature cortical thymocytes", J Neuroimmunol., 2007, 186(1-2), pp. 112-120.
Rudnicka et al., "Rituximab causes a polarization of B cells that augments its therapeutic function in NK-cell—mediated antibody-dependent cellular cytotoxicity", Blood, 2013, 121(23):4694-4702.
Sadat et al., "Nano-pharmaceutical Formulations for Targeted Drug Delivery against HER2 in Breast Cancer", Current Cancer Drug Targets, 2015, 15(1):71-86.
Salven et al., "Enhanced expression of vascular endothelial growth factor in metastatic melanoma", Br. J. Cancer, 1997, 76(7), pp. 930-934.
Sandler et al., "Paclitaxel-carboplatin alone or with bevacizumab for non-small-cell lung cancer", N. Engl. J. Med., 2006, 355:2542-2550.
Sato et al., "Intraepithelial CD8+ tumor-infiltrating lymphocytes and a high CD8+/regulatory T cell ratio are associated with favorable prognosis in ovarian cancer", Proc Natl Acad Sci USA, 2005, 102(51):18538-18543.
Schrama et al., "Antibody targeted drugs as cancer therapeutics, Nature Reviews Drug Discovery", Feb. 2006, 5, pp. 147-159.

Sester et al., "Differences in CMV-specific T-cell levels and long-term susceptibility to CMV infection after kidney, heart and lung transplantation", Am J Transplant., 5(6):1483-1489, Jun. 2005.
Srivastava et al., "Angiogenesis in cutaneous melanoma: pathogenesis and clinical implications", Microsc. Res. Tech., 2003, 60:208-224.
Streit et al., "Angiogenesis, lymphangiogenesis, and melanoma metastasis", Oncogene, 2003, 22, pp. 3172-3179.
Taieb et al., "Chemoimmunotherapy of tumors: Cyclophosphamide synergizes with exosome based vaccines", J. Immunol., Mar. 1, 2006, 176(5):2722-2729.
Tao et al., "Inhibiting the growth of malignant melanoma by blocking the expression of vascular endothelial growth factor using an RNA interference approach", Br. J. Dermatol., 2005, 153:715-724.
Tas et al., "Circulating serum levels of angiogenic factors and vascular endothelial growth factor receptors 1 and 2 in melanoma patients", Melanoma Res., 2006, 16:405-411.
Terheyden et al., "Anti-vascular endothelial growth factor antibody bevacizumab in conjunction with chemotherapy in metastasizing melanoma", J Cancer Res Clin Oncol, 2007, 133(11), pp. 897-901.
Ugurel et al., "Increased serum concentration of angiogenic factors in malignant melanoma patients correlates with tumor progression and survival", J. Clin. Oncol., 2001, 19:577-583.
Vacca et al., "Docetaxel versus paclitaxel for antiangiogenesis", J. Hematother. Stem Cell Res., 2002, 11:103-118.
Varker et al., "A randomized phase 2 trial of bevacizumab with or without daily low-dose interferon alfa-2b in metastatic malignant melanoma", Ann Surg Oncol., 14(8):2367-2376, print Aug. 2007, Epub May 2007.
Vence et al., "Circulating tumor antigen-specific regulatory T cells in patients with metastatic melanoma", Proc Natl Acad Sci USA, 2007, 104(52), pp. 20884-20889.
Wagner et al., "Enhanced drug targeting by attachment of an anti alphav integrin antibody to doxorubicin loaded human serum albumin nanoparticles", Biomaterials., 31(8):2388-2398, Epub Dec. 23, 2009.
Walker et al., "Monitoring immune responses in cancer patients receiving tumor vaccines", Int Rev Immunol., 2003, 22(3-4):283-319.
Wang et al., "Biofunctionalized targeted nanoparticles for therapeutic applications", Expert Opin. Biol. Ther., 2008, 8(8): 1063-1070.
Wang et al., "Paclitaxel at ultra low concentrations inhibits angiogenesis without affecting cellular microtubule assembly", Anti-Cancer Drugs, 2003, vol. 14, Issue 1, pp. 13-19.
Weber, "Review: anti-CTLA-4 antibody ipilimumab: case studies of clinical response and immune-related adverse events", Oncologist, Jul. 2007, 12(7), pp. 864-872.
Wiernik et al., "Phase I trial of taxol given as a 24-hour infusion every 21 days: responses observed in metastatic melanoma", Journal of Clinical Oncology, Aug. 1987, vol. 5, No. 8, pp. 1232-1239.
Wong et al., "Programmed death-1 blockade enhances expansion and functional capacity of human melanoma antigen-specific CTLs", Int. Immunol., 2007, vol. 19, No. 10, pp. 1223-1234.
Wu et al., "Aptamers: Active Targeting Ligands for Cancer Diagnosis and Therapy", Theranostics, 2015, 5(4):322-344.
Yardley et al., "A pilot study of adjuvant nanoparticle albumin-bound (nab) paclitaxel and cyclophosphamide, with trastuzumab in HER2-positive patients, in the treatment of early-stage breast cancer", Breast Cancer Res Treat, 2010, 123:471-475.
Yee et al., "Adoptive T cell therapy using antigen-specific CD8+ T cell clones for the treatment of patients with metastatic melanoma: in vivo persistence, migration, and antitumor effect of transferred T cells", Proc Natl Acad Sci USA, 2002, 99(25):16168-16173.
Yuan et al., "Vascular Permeability in a Human Tumor Xenograft: Molecular Size Dependence and Cutoff Size", Cancer Research, Sep. 1, 1995, 55, pp. 3752-3756.
Zimpfer-Rechner et al., "Randomized phase II study of weekly paclitaxel versus paclitaxel and carboplatin as second-line therapy in disseminated melanoma: a multicentre trial of the Dermatologic Co-operative Oncology Group (DeCOG)", Melanoma Res., 2003, 13:531-536.

(56) References Cited

OTHER PUBLICATIONS

Rao et al., "Combination of Paclitaxel and Carboplatin as Second-Line Therapy for Patients with Metastatic Melanoma", Cancer, Jan. 15, 2006, vol. 106, No. 2, pp. 375-382.
Kratz and Beyer, "Serum proteins as drug carriers of anticancer agents: a review," Drug Deilv., 5(4):281-299, 1998.
European Search Report for Application No. 12781802.9 dated Dec. 18, 2014, 7 pages.
Office Action in U.S. Appl. No. 14/051,849 dated Dec. 19, 2014, 15 pages.
Office Action in U.S. Appl. No. 14/309,617, dated Oct. 1, 2014, 14 pages.
International Preliminary Report on Patentability for PCT/US2013/062638, dated Apr. 16, 2015, 11 pages.
International Search Report and Written Opinion for PCT/US2013/062638, dated Jan. 23, 2014, 19 pages.
Australian Office Action in Application No. 2008224929, dated Jun. 25, 2012, 3 pages.
Australian Office Action in Application No. 2008224929, dated May 31, 2013, 3 pages.
European Office Action for Application No. 09774506.1, dated Nov. 13, 2012, 3 pages.
European Search Report for Application No. 09774506.1, dated Mar. 22, 2012, 12 pages.
European Search Report in Application No. 08743903.0 , dated Feb. 7, 2011, 8 pages.
International Preliminary Report on Patentability for PCT/US2012/037137 dated Nov. 21, 2013, 5 pages.
International Preliminary Report on Patentability in PCT/US2008/057025, dated Sep. 24, 2009, 6 pages.
International Search Report and Written Opinion of international application No. PCT/US2012/037137 dated Sep. 28, 2012, 5 pages.
United States Office Action in U.S. Appl. No. 12/295,834, dated Jan. 27, 2012, 9 pages.
United States Office Action in U.S. Appl. No. 12/295,834, dated Sep. 9, 2011, 7 pages.
United States Office Action in U.S. Appl. No. 13/591,847, dated Sep. 19, 2012, 10 pages.
United States Office Action in U.S. Appl. No. 13/591,847, dated Feb. 19, 2013, 14 pages.
United States Office Action in U.S. Appl. No. 13/591,847, dated Dec. 19, 2013, 28 pages.
United States Office Action in U.S. Appl. No. 12/979,105, dated Oct. 5, 2012, 16 pages.
United States Office Action in U.S. Appl. No. 12/979,105, dated Apr. 11, 2013, 23 pages.
Agarwala et al., "Randomized phase III study of paclitaxel plus carboplatin with or without sorafenib as second-line treatment in patients with advanced melanoma," J. Clin. Oncol., 2007, 25(18S):8510 (Abstract).
Atkins et al., "High-dose recombinant interleukin-2 therapy in patients with metastatic melanoma: long-term survival update," Cancer J Sci Am., 2000, 6 Suppl 1:S11-14.
Atkins, "Interleukin-2: clinical applications," Semin Oncol., 2002, 29(3 Suppl 7):12-27.
Carson et al., "A phase 2 trial of a recombinant humanized monoclonal anti-vascular endothelial growth factor (VEGF) antibody in patients with malignant melanoma," Proceedings of the ASCO vol. 22, No. 2873, General Poster Session, Thirty-Ninth Annual Meeting of the American Society of Clinical Oncology, May 31-Jun. 3, 2003, Chicago, IL, 3 pages.
Chisholm et al., "Response to influenza immunisation during treatment for cancer," Arch Dis Child, 2001, 84(6):496-500.
Chong and Morse "Combining cancer vaccines with chemotherapy," Expert Opin Pharmacother., 2006, 6(16):2813-2820.
Denardo and Coussens, "Inflammation and breast cancer. Balancing immune response: crosstalkbetween adaptive and innate immune cells during breast cancer progression," Breast Cancer Res., 2007, 9(4):212.

ElBayoumi and Torchilin, "Tumor-Targeted Nanomedicines: Enhanced Antitumor Efficacy In vivo of Doxorubicin-Loaded, Long-Circulating Liposomes Modified with Cancer-Specific Monoclonal Antibody," Clin Cancer Res., 2009, 15(6):1973-1980.
Elsadek and Kratz, "Impact of albumin on drug delivery—New applications on the horizon," J of Controlled Release, 2011, 1-25.
Graells et al., "Overproduction of VEGF165 concomitantly expressed with its receptors promotes growth and survival of melanoma cells through MAPK and PI3K signaling," J. Invest. Dermatol., 2004, 123:1151-1161.
Haley and Frenkel, "Nanoparticles for drug delivery in cancer treatment," Urol. Oncol.: Seminars and Original Invest., 2008, 26:57-64.
Jiang and Chess, "Regulation of immune responses by T cells," N Engl J Med., 2006, 354(11): 1166-1176.
Markovic et al., "A reproducible method for the enumeration of functional (cytokine producing) versus non-functional peptide-specific cytotoxic T lymphocytes in human peripheral blood," Clin. Exp. Immunol., 2006, 145:438-447.
Merchan et al., "Increased endothelial uptake of paclitaxel as a potential mechanism for its antiangiogenic effects: potentiation by Cox-2 inhibition," Int. J. Cancer, 2005, 113:490-498.
Middleton et al., "Randomized phase III study of temozolomide versus dacarbazine in the treatment of patients with advanced metastatic malignant melanoma," J. Clin. Oncol., 2000, 18:158-166.
Mimura et al., "Vascular endothelial growth factor inhibits the function of human mature dendritic cells mediated by VEGF receptor-2," Cancer Immunol Immunother., 2007, 56(6):761-770.
Mocellin et al., "Cytokines and immune response in the tumor microenvironment," J Immunother., 2001, 24(5):392-407.
Ng et al., "Influence of formulation vehicle on metronomic taxane chemotherapy: albumin-bound versus cremophor EL-based paclitaxel," Clin. Cancer Res., 2006, 12:4331-4338.
Ng et al., "Taxane-mediated antiangiogenesis In vitro: influence of formulation vehicles and binding proteins," Cancer Res., 2004, 64:821-824.
Oku et al., "Tumor growth modulation by sense and antisense vascular endothelial growth factor gene expression: effects on angiogenesis, vascular permeability, blood volume, blood flow, fluorodeoxyglucose uptake, and proliferation of human melanoma intracerebral xenografts," Cancer Res., 1998, 58:4185-4192.
Parikh and Ellis, "The vascular endothelial growth factor family and its receptors," Hematol. Oncol. Clin. N. Am., 2004, 18:951-971.
Park et al., "Anti-HER2 Immunoliposomes: Enhanced Efficacy Attributable to Targeted Delivery," Clin. Cancer Res., 2002, 8:1172-1181.
Polak et al., "Mechanisms of local immunosuppression in cutaneous melanoma," Br J Cancer, 2007, 96(12):1879-1887.
Porrata and Markovic, "Timely reconstitution of immune competence affects clinical outcome following autologous stem cell transplantation," Clin Exp Med., 2004, 4(2):78-85.
Porrata et al., "Early lymphocyte recovery predicts superior survival after autologous hematopoietic stem cell transplantation in multiple myeloma or non-Hodgkin lymphoma," Blood, 2001, 98(3):579-585.
Powell et al., "Adoptive transfer of vaccine-induced peripheral blood mononuclear cells to patients with metastatic melanoma following lymphodepletion," J Immunol., 2006, 177(9):6527-6539.
Pries and Wollenberg, "Cytokines in head and neck cancer," Cytokine Growth Factor Rev., 2006, 17(3):141-146.
Ribas et al., "Antitumor activity in melanoma and anti-self responses in a phase I trial with the anticytotoxic T lymphocyte-associated antigen 4 monoclonal antibody CP-675,206," J Clin Oncol., 2005, 23(35):8968-8977.
Rosenberg et al., "Tumor progression can occur despite the induction of very high levels of self/tumor antigen-specific CD8+ T cells in patients with melanoma," J. Immunol., 2005, 175(9):6169-6176.
Roy et al., "Tumor associated release of interleukin-10 alters the prolactin receptor and down—regulates prolactin responsiveness of immature cortical thymocytes," J Neuroimmunol., 2007, 186(1-2):112-120.
Salven et al., "Enhanced expression of vascular endothelial growth factor in metastatic melanoma," Br. J. Cancer, 1997, 76:930-934.

(56) References Cited

OTHER PUBLICATIONS

Sato et al., "Intraepithelial CD8+ tumor-infiltrating lymphocytes and a high CD8+/regulatory T cell ratio are associated with favorable prognosis in ovarian cancer," Proc Natl Aead Sci USA, 2005, 102(51):18538-18543.
Streit and Detmar, "Angiogenesis, lymphangiogenesis, and melanoma metastasis," Oncogene, 2003,22:3172-3179.
Taieb et al., "Chemoimmunotherapy of tumors: Cyclophosphamide synergtizes with exoxome based vaccines," J. Immunol., Mar. 1, 2006, 176(5):2722-2729.
Terheyden et al., "Anti-vascular endothelial growth factor antibody bevacizumab in conjunction with chemotherapy in metastasizing melanoma," Journal of Cancer Research and Clinical Oncology, 2007, 133(11): 897-901.
Vence et al., "Circulating tumor antigen-specific regulatory T cells in patients with metastatic melanoma," Proc Natl Acad Sci USA, 2007, 104(52): 20884-20889.
Walker and Disis, "Monitoring immune responses in cancer patients receiving tumor vaccines," Int Rev Immunol., 2003, 22(3-4):283-319.
Wang et al., "Paclitaxel at ultra low concentrations inhibits angiogenesis without affecting cellular microtubule assembly," Anti-Cancer Drugs, 2003, 14:13-19.
Weber, "Review: anti-CTLA-4 antibody ipilimumab: case studies of clinical response and immune related adverse events," Oncologist, 12(7):864-872, Jul. 2007.
Wong et al., "Programmed death-1 blockade enhances expansion and functional capacity of human melanoma antigen-specific CTLs," Int. Immunol., 2007, 19:1223-1234.
Boasberg et al, J Clinical Oncology, 2009, 27: No. 15S, abstract #9061.
Concurrent Infusions, J Oncol Pract. Jul. 2008 ; 4(4) : 171.
Avastin Roche drug label, Sep. 2008.
Abraxane for Injectable Suspension drug label, Sep. 2009.
Perez et al., "Phase 2 Trial of Carboplatin, Weekly Paclitaxel, and Biweekly Bevacizumab in Patients with Unresectable Stage IV Melanoma", Cancer, 2009, vol. 115, Issue 1, pp. 119-127.
U.S. Appl. No. 14/116,619, office action dated Feb. 4, 2015.
U.S. Appl. No. 14/116,619, office action dated Apr. 28, 2016.
U.S. Appl. No. 14/116,619, office action dated Sep. 10, 2015.
U.S. Appl. No. 14/432,979, office action dated May 16, 2018.
U.S. Appl. No. 14/432,979, office action dated Jun. 30, 2016.
U.S. Appl. No. 14/432,979, office action dated Oct. 4, 2017.
U.S. Appl. No. 14/432,979, office action dated Feb. 15, 2016.
U.S. Appl. No. 14/882,327, office action dated May 2, 2011.
U.S. Appl. No. 15/030,567, office action dated Sep. 7, 2016.
U.S. Appl. No. 15/030,568, office action dated May 25, 2017.
U.S. Appl. No. 15/030,568, office action dated Jun. 18, 2018.
U.S. Appl. No. 15/030,568, office action dated Dec. 1, 2017.
U.S. Appl. No. 15/052,336, office action dated Feb. 9, 2018.
U.S. Appl. No. 15/052,623, office action dated Feb. 9, 2018.
U.S. Appl. No. 15/052,623 office action dated May 19, 2017.
U.S. Appl. No. 15/052,623, office action dated Nov. 25, 2016.
U.S. Appl. No, 15/060,967, office action dated Aug. 2, 2016.
U.S. Appl. No. 15/064,396, office action dated Aug. 9, 2017.
U.S. Appl. No. 15/092,433, office action dated Mar. 21, 2018.
U.S. Appl. No. 15/092,433, office action dated Oct. 11, 2017.
U.S. Appl. No. 15/187,672, office action dated May 31, 2017.
U.S. Appl. No. 15/202,115, office action dated Jan. 20, 2017.
U.S. Appl. No. 15/202,115, office action dated Sep. 26, 2016.
U.S. Appl. No. 15/225,428, office action dated Dec. 20, 2017.
U.S. Appl. No. 15/225,504, office action dated Apr. 4, 2017.
U.S. Appl. No. 15/225,504, office action dated Nov. 9, 2016.
U.S. Appl. No. 15/286,006, office action dated Jan. 9, 2017.
U.S. Appl. No. 15/286,006, office action dated Jan. 18, 2018.
U.S. Appl. No. 15/286,006, office action dated May 16, 2017.
U.S. Appl. No. 15/286,024, office action dated Jan. 6, 2017.
U.S. Appl. No. 15/286,024, office action dated May 19, 2017.
U.S. Appl. No. 15/359,569, office action dated Feb. 22, 2017.
U.S. Appl. No. 15/359,569, office action dated Jun. 23, 2017.
U.S. Appl. No. 15/452,669, office action dated May 5, 2017.
U.S. Appl. No. 15/452,669, office action dated Nov. 16, 2017.
Baba, Oleo Science 10(1):15-18 (Jan. 2010).
European Application No, 13843209.1, Extended European Search Report Application No. 13843209.1, dated Sep. 5, 2016.
European Application No. 15806443.6, Extended European Search Report dated Dec. 11, 2017.
Hapa, "What is anti-HER2 antibody tubulin polymerization inhibitor complex T-DM1?," Pharm. Monthly 56(5) 734-739.
International Preliminary Report on Patentability for Application No. PCT/US2015/054295 dated Oct. 3, 2016.
International Preliminary Report on Patentability for Application PCT/US2016/026267, dated Apr. 10, 2018.
International Search Report and Written Opinion for Application No. PCT/US2017/012580, dated Mar. 17, 2017.
International Search Report and Written Opinion for Application No. PCT/US2017/050355 dated Jan. 30, 2018.
Kelly et al. "Shape-Specific, Monodisperse Nano-Molding of Protein Particles," J. Am. Chem. Soc. 130:5438-5439 (2008).
Liang et al., "IFN-alpha regulates NK cell cytotoxicity through STAT1 pathway," Cytokine, Aug. 13, 2003 (Aug. 13, 2013), vol. 23, pp. 190-199.
Makridis, et al., "MHC class I and II antigen expression and interferon ? treatment of human midgut carcinoid tumors," World Journal of Surgery, Aug. 1, 1993 (Aug. 1, 1993), vol. 16, iss. 4, pp. 481-486
Ortaldo et al., "Effects of several species of human leukocyte interferon on cytotoxic activity o fNK cells and monocytes," International Journal of Cancer, Mar. 15, 1983 (Mar. 15, 1983) vol. 31, No. 3, pp. 285-289.
Ouichi, "Antibody delivery—from basics to clinical test—Clinical development of antibody-drug conjugate," Drug Deliv. Sys. 28(5):424-429 (2013).
Soda et al., "Latest topics of new medicine "Albumin-bound paclitaxel, Mol. Respiratory Dis. 17(1):100-103 (Mar. 1, 2013).
U.S. Appl. No. 15/225,542, office action dated Apr. 4, 2017.
U.S. Appl. No. 15/225,542, office action dated Nov. 22, 2016.
Harlow et al., Antibodies: A Laboratory Manual, Cold Spring Harbor Laboratory, New York, 1988 (9 pages).
European Application No. 15809075.3; Extended European Search Report dated Dec. 21, 2017.
U.S. Appl. No. 15/052,623, office action dated Jul. 9, 2018.
U.S. Appl. No. 15/225,504, office action dated Aug. 1, 2018.
U.S. Appl. No. 15/359,569, office action dated Jul. 12, 2018.
U.S. Appl. No. 15/412,564, office action dated Jul. 10, 2018.
U.S. Appl. No. 15/412,610, office action dated Jul. 9, 2018.
Hood et al., Immunology, 1984, Benjamin, N.Y., 2nd edition.
U.S. Appl. No. 15/052,336, office action dated Sep. 4, 2018.
U.S. Appl. No. 15/225,428, office action dated Aug. 14, 2018.
U.S. Appl. No. 15/412,554, office action dated Sep. 27, 2018.
U.S. Appl. No. 15/412,596, office action dated Sep. 4, 2018.
International Preliminary Report on Patentability for Application PCT/US2017/017553, dated Aug. 23, 2018.
Washington University School of Medicine "Phase I/II Study of Abraxane in Recurrent and Refractory Lymphoma", ClinicalTrails. gov, Dec. 6, 2016, 7 pages.
U.S. Appl. No. 15/092,433, office action dated Aug. 10, 2018.
U.S. Appl. No. 15/092,433, office action dated Dec. 12, 2018.
U.S. Appl. No. 15/331,754; office action dated Oct. 11, 2018.
U.S. Appl. No. 15/412,581; office action dated Nov. 13, 2018.
U.S. Appl. No. 15/413,257; office action dated Sep. 25, 2018.
U.S. Appl. No. 15/414,526; office action dated Nov. 16, 2018.
U.S. Appl. No. 15/414,533; office action dated Nov. 19, 2018.
U.S. Appl. No. 15/414,536; office action dated Oct. 11, 2018.
Elst et al. "Epidermal Growth Factor Receptor Expression and Activity in Acute Myeloid Leukemia", Blood 116:3144 (2010), abstract.
International Preliminary Report on Patentability for Application No. PCT/US2016/026270, dated Oct. 18, 2018.
International Preliminary Report on Patentability for Application No. PCT/US2017/012580, dated Jul. 19, 2018.
International Preliminary Report on Patentability for Appiication No. PCT/US2017/023442, dated Oct. 4, 2016.

(56) References Cited

OTHER PUBLICATIONS

International Preliminary Report on Patentability for Application No. PCT/US2017/023443, dated Oct. 4, 2018.
Lloyd et al. "Modelling the human response; performance of a 1011 human antibody repertoire against a broad panel of therapeutically relevant antigens", Protein Eng., Design & Selection 22(3):159-168 (2009).
U.S. Appl. No. 15/452,669, office action dated Nov. 26, 2018.
U.S. Appl. No 14/432,979, office action dated Jan. 7, 2019.
U.S. Appl. No. 15/052,623, office action dated Jan. 7, 2019.
U.S. Appl. No. 15/187,672, office action dated Nov. 28, 2018.
U.S. Appl. No. 15/412,536; office action dated Oct. 1, 2018.
U.S. Appl. No. 15/412,596, office action dated Dec. 27, 2018.
Verma et al. "Effect of surface properties on nanoparticle-cell interactions", Small. 6(1 ): 12-21. (2010).
Robak, T. Emerging monoclonal antibodies and related agents for the treatment of chronic lymphocytic leukemia. Future Oneal. Jan. 2013;(1):69-91, Abstract Only. (Year: 2013).
Reck et al. "Ipilimumab in combination with paclitaxel and carboplatin as first-line therapy in extensive-disease-small-cell lung cancer results from a randomized, double-blind, multicenter phase 2 trial", Ann Oncol, 24(1):75-83 (2013).
Matthey et al. Promising therapeutic targets in neuroblastoma. Clin Cancer Res. May 15, 2012;18(10):2740-53. (Year: 2012).
Iqbal et al. Anti-Cancer Actions of Denosumab. Curr Osteoporos Rep. Dec. 2011;9(4): 173-6. (Year: 2011).
Cheng et al. Molecularly targeted drugs for metastatic colorectal cancer. Drug Des Devel Ther. Nov. 1, 2013;7: 1315-22 (Year: 2013).
Bedu-Addo "Understanding Lyophilization Formulation Development", Pharmaceutical Technology Lyophilization. pp. 10-18 (2004).
U.S. Appl. No. 15/461,288; office action dated Apr. 1, 2019.
U.S. Appl. No. 15/460,552; office action dated Apr. 1, 2019.
U.S. Appl. No. 15/460,699; office action dated Mar. 28, 2019.
U.S. Appl. No. 15/456,399; office action dated Mar. 28, 2019.
U.S. Appl. No. 15/456,377; office action dated Mar. 19, 2019.
U.S. Appl. No. 15/456,382; office action dated Mar. 18, 2019.
U.S. Appl. No. 15/456,391; office action dated Mar. 15, 2019.
U.S. Appl. No. 15/412,610, office action dated Mar. 14, 2019.
U.S. Appl. No. 15/414,526; office action dated Mar. 12, 2019.
U.S. Appl. No. 15/052,336; office action dated Jan. 22, 2019.
U.S. Appl. No. 15/331,754; office action dated Feb. 22, 2019.
U.S. Appl. No. 15/412,581; office action dated Mar. 8, 2019.
U.S. Appl. No. 15/414,533; office action dated Mar. 8, 2019.
U.S. Appl. No. 15/456,395; office action dated Mar. 28, 2019.
International Preliminary Report on Patentability for Application No. PCT/US2017/045643, dated Feb. 14, 2019.
International Preliminary Report on Patentability for Application No. PCT/US2017/049745, dated Mar. 14, 2019.
International Preliminary Report, on Patentability for Application No. PCT/US2017/050137 dated Mar. 21, 2019.
European Application No. 16837869.3, Extended European Search Report dated Apr. 4, 2019.
Anonymous, "Phase I/II Study of Abraxane in Recurrent and Refractory Lymphome", NCT01555853, ClinicalTrials.gov, Jun. 6, 2014 (8 pages).
U.S. Appl. No. 15/092,433, office action dated May 30, 2019.
U.S. Appl. No. 15/225,428, office action dated Jul. 31, 2019.
U.S. Appl. No. 15/225,542; office action dated Jul. 18, 2019.
U.S. Appl. No. 15/286,024, office action dated Aug. 1, 2019.
U.S. Appl. No. 15/359,569, office action dated Jul. 26, 2015.
U.S. Appl. No. 15/430,411, office action dated May 1, 2010.
U.S. Appl. No. 15/452,669, office action dated Jun. 24, 2019.
U.S. Appl. No. 14/456,377; office action dated Jul. 5, 2019.
U.S. Appl. No. 15/456,382; office action dated Jul. 8, 2019.
U.S. Appl. No. 15/456,391; office action dated Jul. 24, 2019.
U.S. Appl. No. 15/458,395, office action dated Aug. 14, 2019.
U.S. Appl. No. 15/456,399; office action dated May 14, 2019.
U.S. Appl. No. 15/460,552; office action dated Aug. 14, 2019.
Beers et al., "CD20 as a Target for Therapeutic Type I and II Monoclonal Antibodies", Seminars in Hematology 47(2):107-114 (2010).
Belldegrun et al. "Human Renal Carcinoma Line Transfected with Interleukin-2 and/or Interferon alpha Gene(s): Implications for Live Cancer Vaccines", J National Cancer Institute 85(3):207-216 (1993).
Buechner "Intralesional interferon alfa-2b in the treatment of basal cell carcinoma", J Am Acad Dermatol 24:731-734 (1991).
Coiffier "The Role of Rituximab in Lympnomas", Rev. Bras. Hematol. Hemoter., 2002, vol. 24, No, 3, ISSN: 1516-8484 (6 pages).
Doveil et al. "Adjuvant Therapy of Stage IIIb Melanoma with Interferon Alfa-2b:Clinical and Immunologic Relevance", Dermatology 191:234-239 (1995).
European Application No. 17736453.6, Extended European Search Report dated Jul. 8, 2019.
International Preliminary Report on Patentability for Application No. PCT/US2017/049746, dated Mar. 14, 2019.
Khallouf et al, "5-Fluorouracil and Interferon-alpha Immunochemotherapy Enhances Immunogenicity of Murine Pancreatic Cancer Through Upregulation of NKG2D Ligands and MHC Class 1", Immunother 35(3):245-253 (2012).
Korthals et al. "Monocyte derived dendritic cells generated by IFN-alpha acquire mature dentritic and natural killer cell properties as shown by gene expression analysis" J Translated Medicine 5:46 (2007) (11 pages).
Package Insert, Campath® (ALEMTUZUMAB), Millennium and ILEX Partners, LP, 13 pages, available May 2001.
U.S. Appl. No. 15/187,672, office action dated Sep. 11, 2019.
U.S. Appl. No. 15/752,155; office action dated Sep. 25, 2019.
Cirstoiu-Hapca et al. "Benefit of anti-HER2-coated paclitaxel-loaded immuno-nanoparticles in the treatment of disseminated ovarian cancer: Therapeutic efficacy and biodistribution in mice", Journal of Controlled Release 144:324-331 (2010).
Liu et al, "Freeze-Drying of Proteins", In: Walkers W., Oldenhof H (eds) Cryopreservation and Freeze-Drying Protocols. Methods in Molecular Biology (Methods and Protocols), vol 1257. Springer, New York, NY; published online Nov. 14 2014.
U.S. Appl. No. 15/460,699; office action dated Aug. 28, 2019.
U.S. Appl. No. 15/461,288; office action dated Aug. 28, 2019.
International Preliminary Report on Patentability for Application No. PCT/US2017/050134 dated Mar. 21, 2019.
European Application No. 17771005.0, Extended European Search Report dated Oct. 17, 2019.
European Application No. 17771006.8, Extended European Search Report dated Oct. 10, 2019.
Anonymous "Paclitaxel Albumin-Stabilized Nanoparticle Formulation and Bevacizumab in Treating Patients With Stage IV Melanoma That Cannot Be Removed by Surgery or Gynecological Cancers", NCT02020707, ClinicalTrials.gov, Dec. 25, 2013 (13 pages).
U.S. Appl. No. 15/225,428, office action dated Dec. 6, 2019.
U.S. Appl. No. 15/430,411; office action dated Oct. 31, 2019.
U.S. Appl. No. 15/675,596; office action dated Dec. 3, 2019.
Reynolds et al. "Phase II Trial of Nanoparticle Albumin-Bound Paclitaxel, Carboplatin, and Bevacizumab in First-Line Patients with Advanced Nonsquamous Non-small Cell Lung Cancer", J Thoracic Oncology 4(12):1537-1543 (2009).

* cited by examiner

Particle Clearance (Δ Fluorescene/Hour)

Rate of Tumor Clearance Compared to Background (Tumor/Background)

| | |
|---|---|
| Abraxane | 2.717127608 |
| AB160 w/o Pre Treating | 1.371746888 |
| AB160 w/ Pre Treatment | 1.407543698 |

Tumor Clearance Rate Relative to Abraxane

| | |
|---|---|
| Abraxane | 1 |
| AB160 w/o Pre Treating | 0.504851846 |
| AB160 w/ Pre Treatment | 0.51802635 |

METHODS OF TREATING CANCER USING COMPOSITIONS OF ANTIBODIES AND CARRIER PROTEINS WITH ANTIBODY PRETREATMENT

This application claims benefit of the filing dates of provisional application Nos. 62/247,470 filed Oct. 28, 2015 and 62/252,377 filed Nov. 6, 2015, the disclosures of which are incorporated herein by reference.

FIELD OF THE INVENTION

This disclosure relates to novel methods and kits for treating cancer using vascular endothelial growth factor (VEGF) antibodies and carrier protein/VEGF antibody complexes.

STATE OF THE ART

Chemotherapy remains a mainstay for systemic therapy for many types of cancer, including melanoma. Most chemotherapeutics are only slightly selective to tumor cells, and toxicity to healthy proliferating cells can be high (Allen T M. (2002) *Cancer* 2:750-763), often requiring dose reduction and even discontinuation of treatment. In theory, one way to overcome chemotherapy toxicity issues as well as improve drug efficacy is to target the chemotherapy drug to the tumor using antibodies that are specific for proteins selectively expressed (or overexpressed) by tumors cells to attract targeted drugs to the tumor, thereby altering the biodistribution of the chemotherapy and resulting in more drug going to the tumor and less affecting healthy tissue. Despite 30 years of research, however, specific targeting rarely succeeds in the therapeutic context.

Conventional antibody dependent chemotherapy (ADC) is designed with a toxic agent linked to a targeting antibody via a synthetic protease-cleavable linker. The efficacy of such ADC therapy is dependent on the ability of the target cell to bind to the antibody, the linker to be cleaved, and the uptake of the toxic agent into the target cell. Schrama, D. et al. (2006) *Nature reviews. Drug discovery* 5:147-159.

Antibody-targeted chemotherapy promised advantages over conventional therapy because it provides combinations of targeting ability, multiple cytotoxic agents, and improved therapeutic capacity with potentially less toxicity. Despite extensive research, clinically effective antibody-targeted chemotherapy remains elusive: major hurdles include the instability of the linkers between the antibody and chemotherapy drug, reduced tumor toxicity of the chemotherapeutic agent when bound to the antibody and the inability of the conjugate to bind and enter tumor cells. In addition, these therapies did not allow for control over the size of the antibody-drug conjugates.

It was recently discovered that nanoparticle complexes of a carrier protein-bound chemotherapeutic and antibody have superior therapeutic efficacy, including in humans, than either the chemotherapeutic or antibody delivered alone or sequentially, resulting in a significantly reduced tumor size. See, PCT Application No. PCT/US15/54295. It is contemplated that these nanoparticles have improved targeting of the chemotherapeutics to the tumor, and that this targeting may be mediated, at least in part, by the bound antibody. It is further contemplated that the carrier protein-bound chemotherapeutic increases the targeting of the antibody to the tumor or that the existence of the complex shows greater stability in vivo than chemotherapeutic alone.

Even still, there remains a need in the art to improve the efficacy of cancer therapeutics.

SUMMARY

This invention is directed, in part, on the discovery that treatment of a cancer expressing vascular endothelial growth factor (VEGF) with an anti-VEGF antibody composition enhances the effectiveness of carrier-bound (e.g., albumin) chemotherapeutic/anti-VEGF antibody nanoparticles containing a therapeutically effective amount of the chemotherapeutic. Preferably, such anti-VEGF antibodies are administered prior to treatment with such nanoparticles. Accordingly, in one aspect, provided herein are methods for treating a patient suffering from a cancer which expresses VEGF wherein said patient is treated with a sub-therapeutic amount of an anti-VEGF antibody and carrier-bound (e.g., albumin) chemotherapeutic/anti-VEGF antibody nanoparticle complexes containing a therapeutically effective amount of the chemotherapeutic such that the administration of said sub-therapeutic amount of the anti-VEGF antibody enhances the efficacy of said nanoparticle complexes. It is contemplated that administration of a sub-therapeutic amount of the anti-VEGF antibody enhances the efficacy of the nanoparticle complexes, at least in part, by clearing the blood stream of at least some undesired, non-tumor VEGF targets. Treatment with a sub-therapeutic amount of anti-VEGF antibody may allow for greater targeting of the nanoparticle complexes to the tumor, decrease the amounts of the chemotherapeutic/antibody complexes administered to a patient, or both.

In another aspect, provided herein are methods for enhancing the efficacy of albumin-bound chemotherapeutic/anti-VEGF antibody nanoparticle complexes by administering the albumin-bound chemotherapeutic/anti-VEGF antibody nanoparticle complexes about 0.5 to 48 hours after pretreatment of a patient with a sub-therapeutic amount of anti-VEGF antibody.

Preferably, such nanoparticle complexes are administered about 24 hours after the sub-therapeutic amount of anti-VEGF antibody.

In another aspect, provided herein are methods for enhancing the therapeutic outcome in a patient suffering from a cancer expressing soluble VEGF which patient is selected to be treated with nanoparticles comprising albumin-bound paclitaxel and anti-VEGF antibodies wherein said antibodies of the nanoparticles are integrated onto and/or into said nanoparticles which method comprises treating said patient with a sub-therapeutic amount of said anti-VEGF antibody prior to any subsequent treatment with the nanoparticles.

In another aspect, provided herein are methods for enhancing the therapeutic outcome in a patient suffering from a cancer overexpressing soluble VEGF, said method comprising treating the patient with a sub-therapeutic amount of said anti-VEGF antibody and co-treating said patients with an effective amount of nanoparticles comprising albumin-bound paclitaxel and anti-VEGF antibodies wherein said antibodies of the nanoparticles are integrated onto and/or into said nanoparticles.

In one embodiment, the chemotherapeutic is paclitaxel.

In one embodiment, the anti-VEGF antibody is bevacizumab or a biosimilar version thereof.

In one embodiment, the sub-therapeutic amount of anti-VEGF antibody is selected from an amount consisting of about 1%, about 5%, about 10%, about 15%, about 20%, about 25%, about 30%, about 35%, about 40%, about 45%, about 50%, about 55% or about 60% of the therapeutic dosage of anti-VEGF antibody. It is contemplated that administration of the sub-therapeutic amount of anti-VEGF antibody preferentially blocks circulating VEGF with minimal blocking of VEGF associated with a tumor). In some embodiments, the sub-therapeutic amount of anti-VEGF to be administered to the patient is determined by analyzing the level of circulating VEGF in the blood.

In one embodiment, the sub-therapeutic amount of anti-VEGF antibody is administered from between about 30 minutes to about 48 hours prior to administration of the albumin-bound chemotherapeutic/anti-VEGF antibody nanoparticle complexes.

In one embodiment, the target of said nanoparticle complexes is a solid cancer.

In other aspects, provided herein are unit-dose formulations of an anti-VEGF antibody, for example, bevacizumab or a biosimilar version thereof, which formulation comprises from about 1% to about 60% of a therapeutic dose of said antibody wherein said formulation is packaged so as to be administered as a unit dose.

In some embodiments, the formulation comprises from about 5% to about 20% of a therapeutic dose of bevacizumab or a biosimilar version thereof. The therapeutic dose for bevacizumab for a given approved indication, e.g., treatment for metastatic colorectal cancer, non-squamous non-small cell lung cancer, metastatic breast cancer, glioblastoma, and metastatic renal cell carcinoma, is recited in the prescribing information. In each case the therapeutic dose is from 5 to 15 mg/kg and preferably a subtherapeutic dose ranges from 5% to 20% of the therapeutic dose. In such a preferred embodiment such a subtherapeutic dose would range from 0.25 mg/kg to 3 mg/kg, more preferably from 0.5 to 2 mg/kg.

In other aspects, provided herein are kits comprising: (a) an amount of an albumin-bound chemotherapeutic/anti-VEGF antibody complexes, (b) a unit dose of a sub-therapeutic amount of anti-VEGF antibody, and optionally (c) instructions for use.

In one embodiment, the albumin-bound chemotherapeutic/anti-VEGF antibody complexes of the kits are lyophilized.

An embodiment of the invention includes a method for increasing the duration of tumor uptake of a chemotherapeutic agent by administering the chemotherapeutic agent in a nanoparticle comprising a carrier protein and the chemotherapeutic agent and having surface complexation with an antibody, e.g., an antibody that specifically binds to an antigen on or shed by the tumor. In some embodiments the subject receives a subtherapeutic amount of the antibody prior to or concurrently with such nanoparticles.

BRIEF DESCRIPTION OF THE DRAWINGS

The following figures are representative only of the invention and are not intended as a limitation. For the sake of consistency, the nanoparticles of this invention using albumin-bound paclitaxel (e.g., ABRAXANE®) and bevacizumab employ the acronym "AB" and the number after AB such as AB160 is meant to confer the average particle size of these nanoparticles (in nanometers).

FIG. 7 depicts fluorescence over time of AlexaFluor 750 labeled nanoparticles in the tumors of mice treated with ABRAXANE® or AB160 with or without a pretreatment with bevacizumab.

DETAILED DESCRIPTION

Figure 1A:
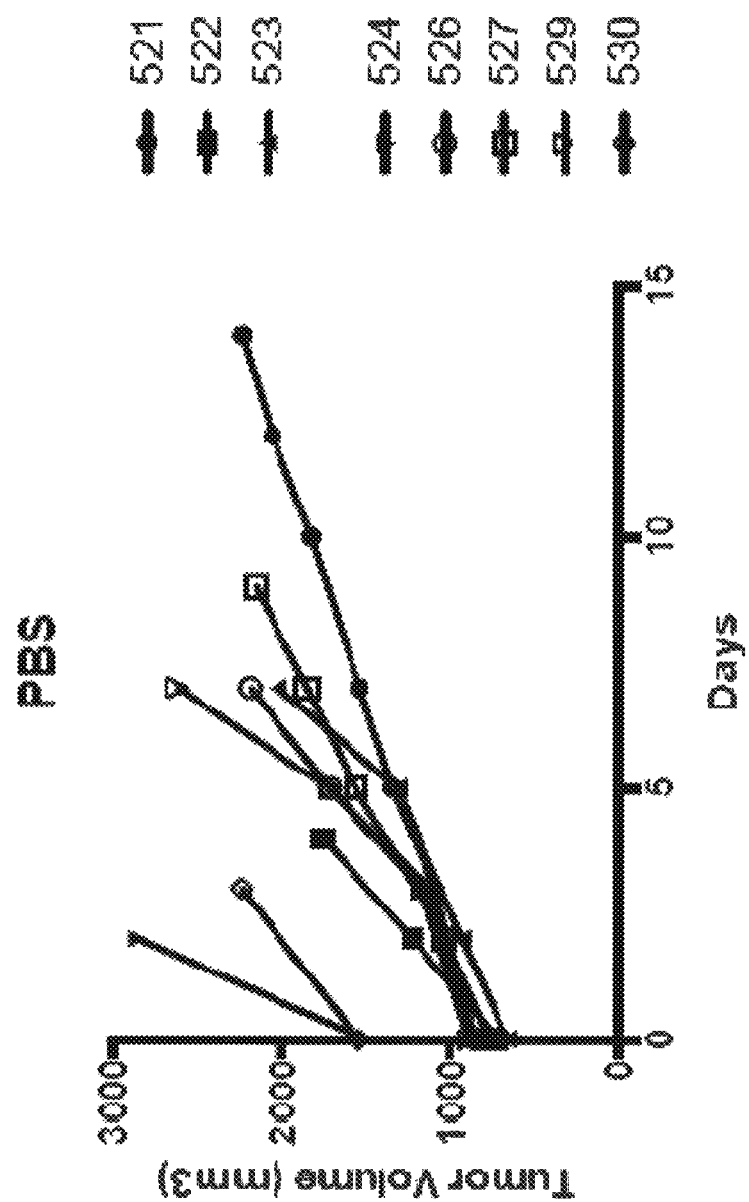
FIGS. 1A-E show in vivo testing of athymic nude mice injected with 1×106 A375 human melanoma cells in the right flank and treated with (FIG. 1A) PBS, (FIG. 1B) 12 mg/kg BEV, (FIG. 1C) 30 mg/kg ABX, (FIG. 1D) AB160, or (FIG. 1E) pretreated with 1.2 mg/kg BEV and, 24 hr later, AB160. Data is represented at day 15-post treatment, or longer, as tumor volume in $mm^3$.
Figure 1B:
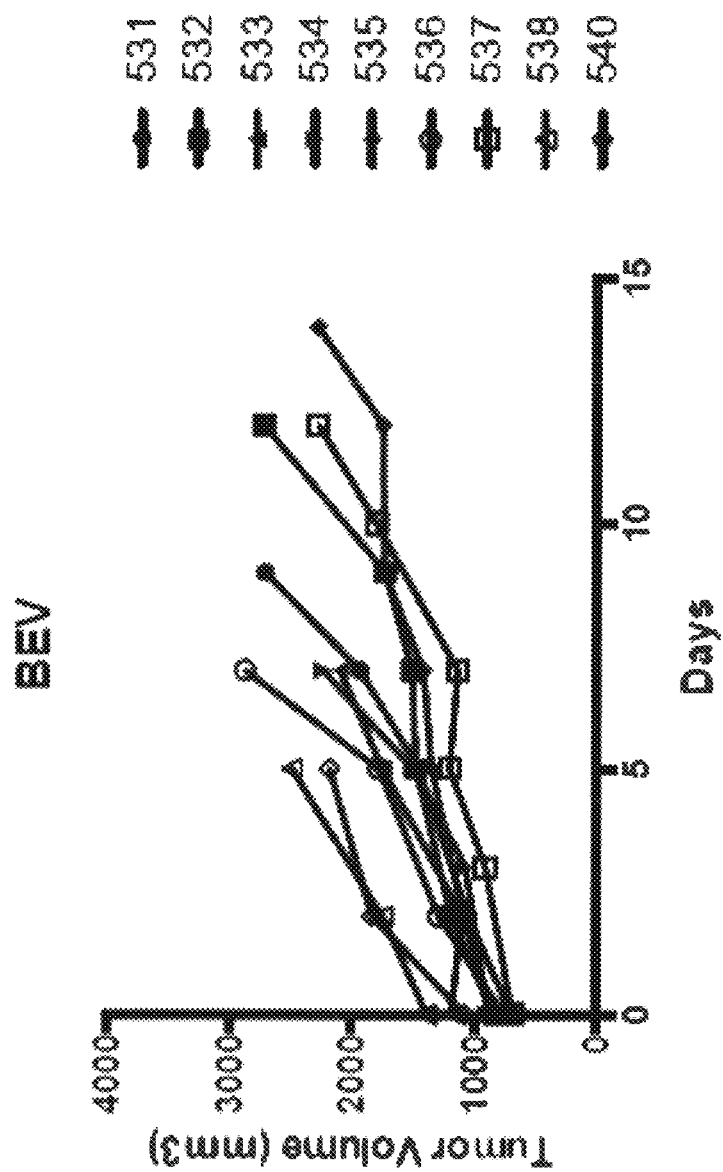
Figure 1C:
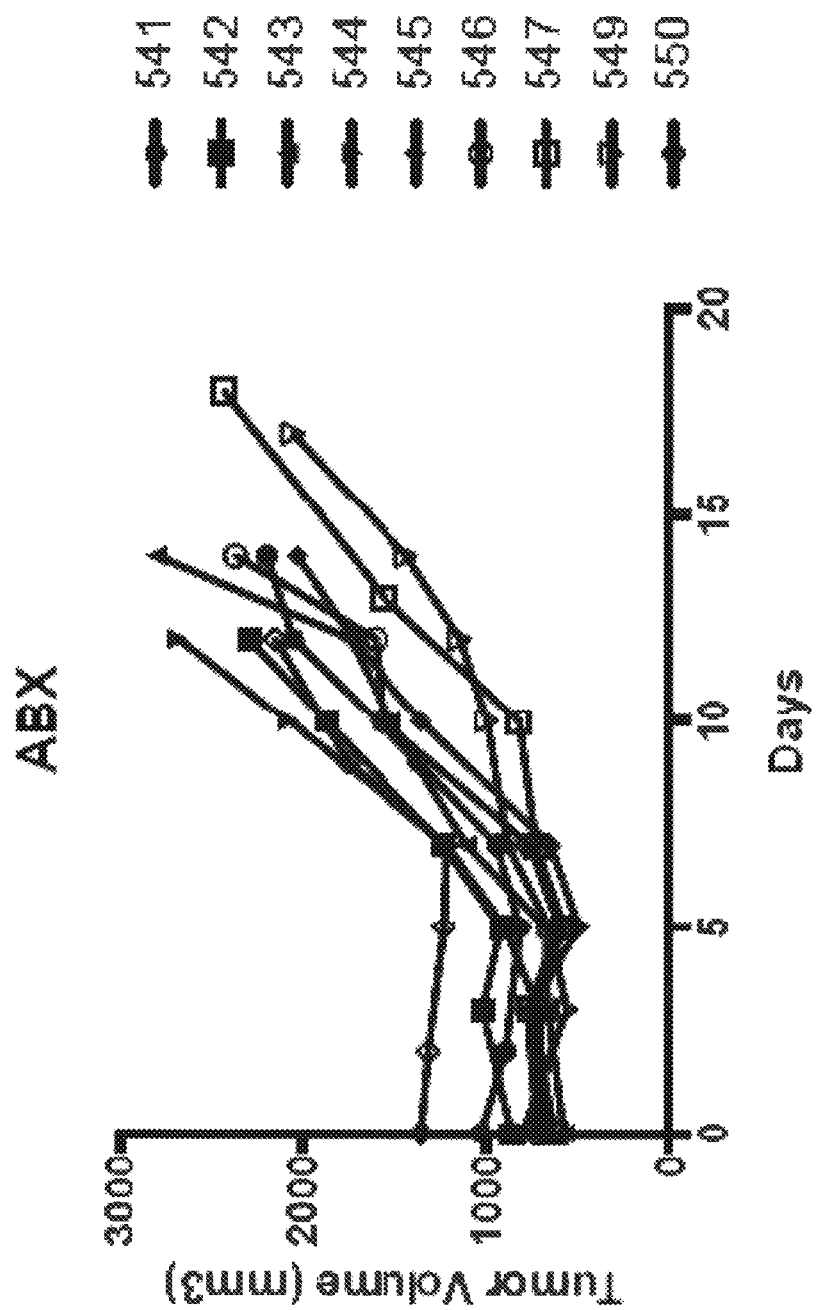
Figure 1D:
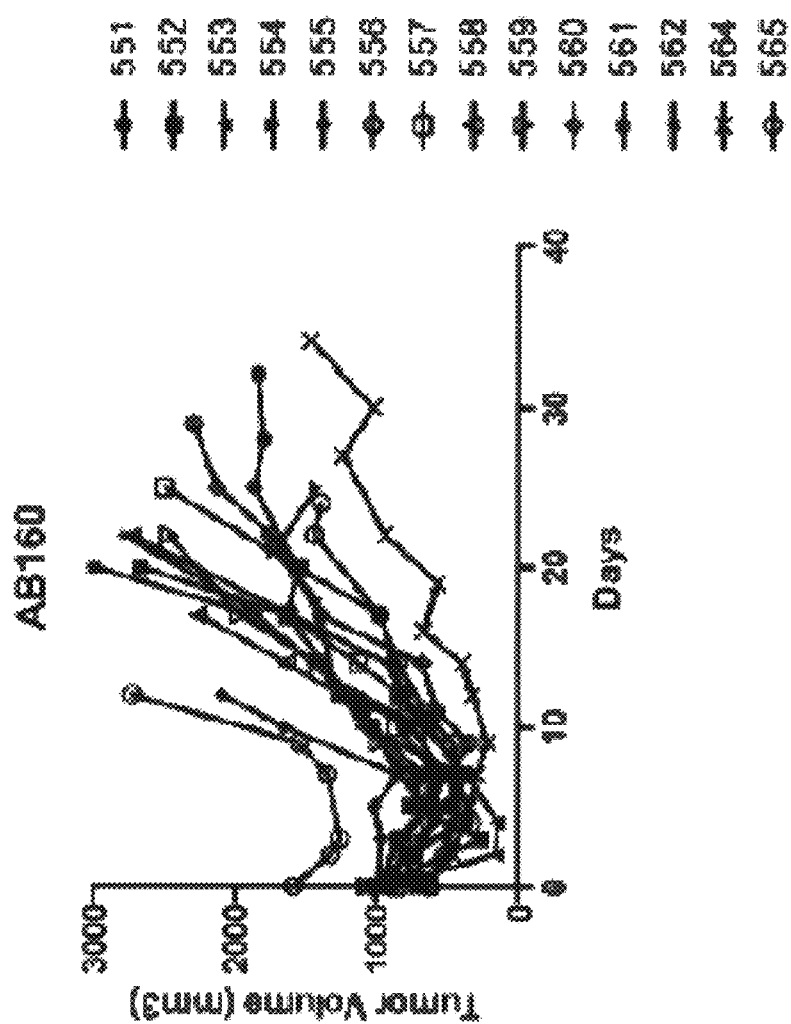
Figure 1E:
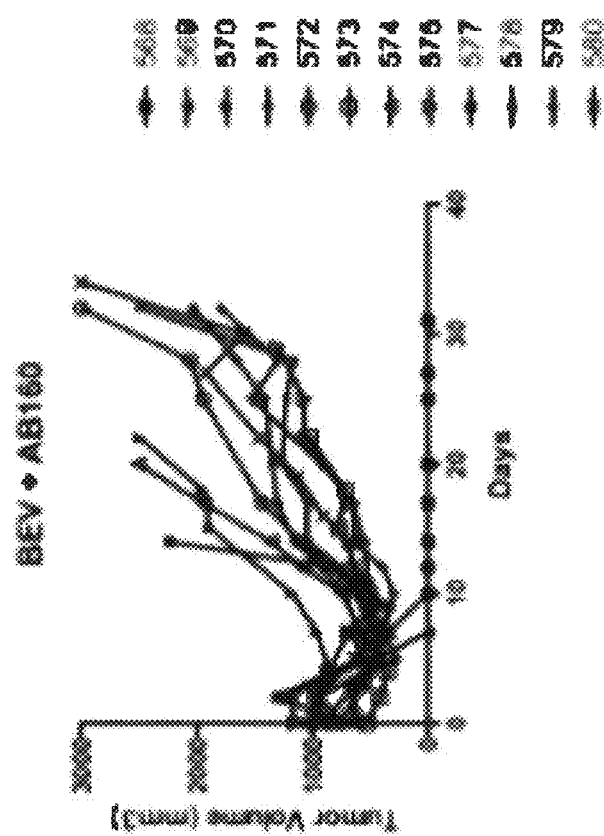

After reading this description it will become apparent to one skilled in the art how to implement the invention in various alternative embodiments and alternative applications.

However, all the various embodiments of the present invention will not be described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Titles or subtitles may be used in the specification for the convenience of a reader, which are not intended to influence the scope of the present invention.

Definitions

Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to a dose amount means that the dose may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, the term "sub-therapeutic" is used to describe an amount of antibody that is below the amount of antibody conventionally used to treat a cancer. For example, a sub-therapeutic amount is an amount less than that defined by the manufacturer as being required for therapy.

The term "nanoparticle" as used herein refers to particles having at least one dimension which is less than 5 microns. In preferred embodiments, such as for intravenous administration, the nanoparticle is less than 1 micron. For direct administration, e.g., into a tumor, the nanoparticle can be larger. Even larger particles are expressly contemplated by the invention.

In a population of particles, the size of individual particles are distributed about a mean. Particle sizes for the population can therefore be represented by an average, and also by percentiles. D50 is the particle size below which 50% of the particles fall. 10% of particles are smaller than the D10 value and 90% of particles are smaller than D90. Where unclear, the "average" size is equivalent to D50. So, for example, AB160 refers to nanoparticles having an average size of 160 nanometers.

The term "nanoparticle" may also encompass discrete multimers of smaller unit nanoparticles. For example, a 320 nm particle comprises a dimer of a unit 160 nm nanoparticle. For 160 nm nanoparticles, multimers would therefore be approximately 320 nm, 480 nm, 640 nm, 800 nm, 960 nm, 1120 nm, and so on as determined by a Mastersizer 2000 (available from Malvern Instruments Ltd, Wocestershire, UK) as described in PCT/US15/54295.

The term "biosimilar" as used herein refers to a biopharmaceutical which is deemed to be comparable in quality, safety, and efficacy to a reference product marketed by an innovator company (Section 351(i) of the Public Health Service Act (42 U.S.C. 262(i)).

The term "carrier protein" as used herein refers to proteins that function to transport antibodies and/or therapeutic agents. The antibodies of the present disclosure can reversibly bind to the carrier proteins. Exemplary carrier proteins are discussed in more detail below.

The term "core" as used herein refers to central or inner portion of the nanoparticle which may be comprised of a carrier protein, a carrier protein and a therapeutic agent, or other agents or combination of agents. In some embodiments, a hydrophobic portion of the antibody may be incorporated into the core.

As used herein, the term "enhancing the therapeutic outcome" and the like relative to a cancer patient refers to a slowing or diminution of the growth of cancer cells or a solid tumor, or a reduction in the total number of cancer cells or total tumor burden.

The term "therapeutic agent" as used herein means an agent which is therapeutically useful, e.g., an agent for the treatment, remission or attenuation of a disease state, physiological condition, symptoms, or etiological factors, or for the evaluation or diagnosis thereof. A therapeutic agent may be a chemotherapeutic agent, for example, mitotic inhibitors, topoisomerase inhibitors, steroids, anti-tumor antibiotics, antimetabolites, alkylating agents, enzymes, proteasome inhibitors, or any combination thereof.

The term "antibody" or "antibodies" as used herein refers to immunoglobulin molecules and immunologically active portions of immunoglobulin molecules (i.e., molecules that contain an antigen binding site that immuno-specifically bind an antigen). The term also refers to antibodies comprised of two immunoglobulin heavy chains and two immunoglobulin light chains as well as a variety of forms including full length antibodies and portions thereof including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984); Harlow and Lane, Antibodies. A Laboratory Manual, Cold Spring Harbor Laboratory (1988); Hunkapiller and Hood, Nature, 323, 15-16 (1986), which are incorporated herein by reference). The antibody may be of any type (e.g., IgG, IgA, IgM, IgE or IgD). Preferably, the antibody is IgG. An antibody may be non-human (e.g., from mouse, goat, or any other animal), fully human, humanized, or chimeric. In an embodiment the antibody is an exogenous antibody. An exogenous antibody is an antibody not naturally produced in a mammal, e.g. in a human, by the mammalian immune system.

The term "dissociation constant," also referred to as "Kd," refers to a quantity expressing the extent to which a particular substance separates into individual components (e.g., the protein carrier, antibody, and optional therapeutic agent).

The terms "lyophilized," "lyophilization" and the like as used herein refer to a process by which the material (e.g., nanoparticles) to be dried is first frozen and then the ice or frozen solvent is removed by sublimation in a vacuum environment. An excipient is optionally included in pre-lyophilized formulations to enhance stability of the lyophilized product upon storage. In some embodiments, the nanoparticles can be formed from lyophilized components (carrier protein, antibody and optional therapeutic) prior to use as a therapeutic. In other embodiments, the carrier protein, antibody, and optional therapeutic agent are first combined into nanoparticles and then lyophilized. The lyophilized sample may further contain additional excipients.

The term "buffer" encompasses those agents which maintain the solution pH in an acceptable range prior to lyophilization and may include succinate (sodium or potassium), histidine, phosphate (sodium or potassium), Tris(tris(hydroxymethyl)aminomethane), diethanolamine, citrate (sodium) and the like. The buffer of this invention has a pH in the range from about 5.5 to about 6.5; and preferably has a pH of about 6.0. Examples of buffers that will control the pH in this range include succinate (such as sodium succinate), gluconate, histidine, citrate and other organic acid buffers.

The term "pharmaceutical formulation" refers to preparations which are in such form as to permit the active ingredients to be effective, and which contains no additional components which are toxic to the subjects to which the formulation would be administered.

"Pharmaceutically acceptable" excipients (vehicles, additives) are those which can reasonably be administered to a subject mammal to provide an effective dose of the active ingredient employed.

"Reconstitution time" is the time that is required to rehydrate a lyophilized formulation into a solution.

A "stable" formulation is one in which the protein therein essentially retains its physical stability and/or chemical stability and/or biological activity upon storage.

The term "epitope" as used herein refers to the portion of an antigen which is recognized by an antibody. Epitopes include, but are not limited to, a short amino acid sequence or peptide (optionally glycosylated or otherwise modified) enabling a specific interaction with a protein (e.g., an antibody) or ligand. For example, an epitope may be a part of a molecule to which the antigen-binding site of an antibody attaches.

The term "treating" or "treatment" covers the treatment of a disease or disorder (e.g., cancer), in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments "treating" or "treatment" refers to the killing of cancer cells.

The term "kill" with respect to a cancer treatment is directed to include any type of manipulation that will lead to the death of that cancer cell or at least a portion of a population of cancer cells.

The term "dose" refers to an amount of antibody given to a patient in need thereof. The attending clinician will select an appropriate dose from the range based on the patient's weight, age, health, stage of cancer, level of circulating VEGF, and other relevant factors, all of which are well within the skill of the art.

The term "unit dose" refers to a dose of the antibody that is given to the patient to provide a desired result. In some instances, the unit dose is sold in a sub-therapeutic formulation (e.g., 10% the therapeutic dose). The unit dose may be administered as a single dose or a series of subdoses. The therapeutic dose for an antibody for a given FDA-approved indication is recited in the prescribing information, for example the therapeutic dose of bevacizumab is 5 mg/kg to 15 mg/kg depending on the condition, and preferably a subtherapeutic dose ranges from 5% to 20% of the therapeutic dose. In such a preferred embodiment such a subtherapeutic dose would range from 0.25 mg/kg to 3 mg/kg, more preferably from 0.5 to 2 mg/kg. The therapeutic dose for an antibody for a given indication where the antibody is not yet FDA approved or the antibody is not yet approved for that indication, will be the amount the correlates to the therapeutic that has been approved for other indications, and thus the subtherapeutic dose for the non-FDA approved indications is readily calculated as a percent of the therapeutic dose (e.g., 10% of the therapeutic dose). For example, the therapeutic dose and therefore the subtherapeutic dose of an antibody for the treatment of metastatic melanoma correlates to the therapeutic dose for metastatic cancers in general that has been approved.

Additionally, some terms used in this specification are more specifically defined below.

Overview

The current invention is predicated, in part, on the surprising discovery that treatment of a cancer in a patient with an anti-VEGF antibody composition together with albumin-bound chemotherapeutic/anti-VEGF antibody nanoparticle complexes provides for unexpectedly improved therapeutic outcomes.

As will be apparent to the skilled artisan upon reading this disclosure, the present disclosure relates to methods for treating a patient suffering from a cancer by treating the patient with a sub-therapeutic amount of an anti-VEGF antibody and albumin-bound chemotherapeutic/anti-VEGF antibody nanoparticle complexes containing a therapeutically effective amount of the chemotherapeutic.

Anti-VEGF Antibodies

In some embodiments, the anti-VEGF antibody is bevacizumab or a biosimilar version thereof.

Bevacizumab (AVASTTN®, Roche, USA) is a humanized monoclonal antibody that inhibits angiogenesis by blocking the action of vascular endothelial growth factor (VEGF). As such, bevacizumab can slow the growth of new blood vessels in tumors thereby inhibiting the tumors ability to grow. Bevacizumab has been used to treat various cancers including, non-small cell lung cancer (NSCLC), metastatic colorectal cancer (mCRC), platinum-resistant ovarian cancer (prOC), advanced cervical cancer (CC), metastatic renal cell carcinoma (mRCC), and recurrent glioblastoma (rGBM). Several biosimilar versions of bevacizumab are currently being developed including ABP 215 (Amgen/Allergen, USA), BCD-021 (Biocad, Russia), BI 695502 (Boehringer Ingelheim, Germany), and PF-06439535 (Pfizer, USA), among others.

In some embodiments, the sub-therapeutic amount of anti-VEGF antibody is selected from an amount consisting of about 1%, about 5%, about 10%, about 15%, about 20%, about 25%, about 30%, about 35%, about 40%, about 45%, about 50%, about 55% or about 60% of the therapeutic dosage of anti-VEGF antibody.

In some embodiments, the sub-therapeutic amount of anti-VEGF antibody is an amount which preferentially blocks circulating VEGF without blocking VEGF associated with tumor.

Complexes

Carrier protein-bound chemotherapeutic/anti-VEGF antibody complexes and methods of preparing the complexes are described, for example, in U.S. Provisional App. No. 62/060,484, filed Oct. 6, 2014; and U.S. Provisional Patent Application Nos. 62/206,770; 62/206,771; and 62/206,772 filed Aug. 18, 2015, as well as PCT Publication No. PCT/US15/54295, filed Oct. 6, 2015. The contents of each of these applications are specifically incorporated by reference in their entireties. Example 1 below provides one example of a detailed protocol for making such complexes.

In some embodiments, the anti-VEGF antibody is bevacizumab or a biosimilar version thereof. In some embodiments, the antibodies are a substantially single layer of antibodies on all or part of the surface of the nanoparticle.

In some embodiments, the at least one chemotherapeutic agent is selected from the group consisting of abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, paclitaxel, pazopanib, pemetrexed, picoplatin, romidepsin, satraplatin, sorafenib, vemurafenib, sunitinib, teniposide, triplatin, vinblastine, vinorelbine, vincristine, and cyclophosphamide. In preferred embodiments, the chemotherapeutic is paclitaxel.

In some embodiments, the nanoparticle sizes are between 200 and 800 nm, including 200, 300, 400, 500, 600, 700 or 800 nm. In other embodiments, the nanoparticles are larger, e.g. from greater than 800 nm to about 3.5 µm. In some embodiments, the particles are multimers of nanoparticles. In some embodiments the nanoparticles have average particle sizes of about 160 nm to about 225 nm either freshly made or after lyophilization and resuspension in an aqueous solution suitable for injection.

Treatment Methods

In one aspect is provided a method for treating a patient suffering from a cancer which expresses VEGF wherein said patient is treated with a sub-therapeutic amount of an anti-VEGF antibody and albumin-bound chemotherapeutic/anti-VEGF antibody nanoparticle complexes containing a therapeutically effective amount of the chemotherapeutic such that the administration of said sub-therapeutic amount of the anti-VEGF antibody enhances the efficacy of said nanoparticle complexes.

For the sake of clarification, "co-treatment" refers to treatment of the cancer expressing VEGF (a soluble cytokine) with an anti-VEGF antibody prior, concurrent or immediately after administration of the albumin-bound chemotherapeutic/anti-VEGF antibody complex provided that the anti-VEGF antibody is capable of preferentially binding soluble VEGF.

In one embodiment, the anti-VEGF antibody is administered in a sub-therapeutic dose prior to the nanoparticle complex. In this embodiment, the administration of the anti-VEGF antibody occurs about 0.5 to 48 hours prior to administration of the nanoparticle complexes.

In another embodiment, the anti-VEGF antibody composition is administered between 0.5 hours prior to and up to 0.5 hours after administration of the nanoparticle complexes. In this embodiment, it is contemplated that such administration will nevertheless result in binding of some of the circulating VEGF by the antibody composition.

In yet another embodiment, the antibody composition can be administered up to 2 hours post administration of the nanoparticle complexes.

In a preferred aspect, there is provided methods for enhancing the efficacy of albumin-bound chemotherapeutic/anti-VEGF antibody nanoparticle complexes by administering the albumin-bound chemotherapeutic/anti-VEGF antibody nanoparticle complexes about 0.5 to 48 hours after pretreatment of a patient with a sub-therapeutic amount of anti-VEGF antibody. Preferably, such nanoparticle complexes are administered about 24 hours after the sub-therapeutic amount of anti-VEGF antibody.

In another aspect, there is provided methods for enhancing the therapeutic outcome in a patient suffering from a cancer expressing soluble VEGF which patient is selected to be treated with nanoparticles comprising albumin-bound paclitaxel and anti-VEGF antibodies wherein said antibodies of the nanoparticles are integrated onto and/or into said nanoparticles which method comprises treating said patient with a sub-therapeutic amount of said anti-VEGF antibody prior to any subsequent treatment with the nanoparticles.

In another aspect, there is provided methods for enhancing the therapeutic outcome in a patient suffering from a cancer overexpressing soluble VEGF, said method comprising treating the patient with a sub-therapeutic amount of said anti-VEGF antibody and co-treating said patients with an effective amount of nanoparticles comprising albumin-bound paclitaxel and anti-VEGF antibodies wherein said antibodies of the nanoparticles are integrated onto and/or into said nanoparticles.

In another aspect, there is provided a method for enhancing the therapeutic outcome in a patient suffering from a cancer expressing soluble VEGF which patient is to be treated with nanoparticles comprising albumin-bound paclitaxel and anti-VEGF antibodies wherein said antibodies of the nanoparticles are integrated onto and/or into said nanoparticles which method comprises treating said patient with a sub-therapeutic amount of said anti-VEGF antibody within +/−0.5 hours of administration of said nanoparticles.

In another aspect is provided a method for enhancing the therapeutic outcome in a patient suffering from a cancer overexpressing soluble VEGF which patient has been treated with a sub-therapeutic amount of said anti-VEGF antibody said method comprising treating said patients with an effective amount of nanoparticles comprising albumin-bound paclitaxel and anti-VEGF antibodies wherein said antibodies of the nanoparticles are integrated onto and/or into said nanoparticle antibody within +/−0.5 hours of administration of said antibodies.

The patient may be co-treated with a sub-therapeutic amount of an anti-VEGF antibody and albumin-bound chemotherapeutic/anti-VEGF antibody complex.

In some embodiments the anti-VEGF antibody is administered prior to the albumin-bound chemotherapeutic/anti-VEGF antibody complex, for example, the anti-VEGF antibody can be administered minutes, hours or days prior to administration of the albumin-bound chemotherapeutic/anti-VEGF antibody complex. In some embodiments, the anti-VEGF antibody is administered between about 5 to about 59 minutes, about 10 to about 50 minutes, about 15 to about 45 minutes, about 20 to about 40 minutes, about 25 to about 35 minutes prior to administration of the albumin-bound chemotherapeutic/anti-VEGF antibody complex. In other embodiments, the anti-VEGF antibody can be administered about 1 hour, about 2 hours, about 3 hours, about 4 hours, about 5 hours, about 6 hours, about 12 hours, about 24 hours, about 48 hours, about 72 hours, or longer prior to administration of the albumin-bound chemotherapeutic/anti-VEGF antibody complex. In other embodiments, the anti-VEGF antibody can be administered about 1 day, about 2 days, about 3 days, about 4 days, about 5 days, about 6 days, about 7 days, about 10 days, about 12 days, about 15 days, or longer prior to administration of the albumin-bound chemotherapeutic/anti-VEGF antibody complex.

In some embodiments, the anti-VEGF antibody can be administered concurrently with administration of the albumin-bound chemotherapeutic/anti-VEGF antibody complex, for example, within 10 minutes or less of each other.

In other embodiments, the anti-VEGF antibody can be administered subsequent to administration of the albumin-bound chemotherapeutic/anti-VEGF antibody complex, for example, within 2 hours after administration of the albumin-bound chemotherapeutic/anti-VEGF antibody complex, provided that the subsequent administration allows the antibody to preferentially bind the soluble VEGF.

Cancers or tumors that can be treated by the compositions and methods described herein include, but are not limited to: biliary tract cancer; brain cancer, including glioblastomas and medulloblastomas; breast cancer; cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepatocarcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyo sarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors include breast cancer, lymphoma, multiple myeloma, and melanoma.

Formulations

In one aspect, the anti-VEGF is a unit-dose formulation of an anti-VEGF antibody which formulation comprises from about 1% to about 60% of a therapeutic dose of said antibody wherein said formulation is packaged so as to be administered as a unit dose. In an aspect of the invention, the unit-dose formulation of an anti-VEGF antibody comprises about 10% of a therapeutic dose of said antibody. For example 10% of a therapeutic dose of an anti-VEGF antibody, e.g., bevacizumab, may be 0.5 mg/kg to 5 mg/kg.

The unit-dose formulation of an anti-VEGF antibody can be about 1% to about 60%, about 5% to about 50%, about 10% to about 40%, about 15% to about 30%, about 20% to about 25%, of a therapeutic dose of the anti-VEGF antibody. Contemplated values include any value, subrange, or range within any of the recited ranges, including endpoints.

In some embodiments, the anti-VEGF antibody is bevacizumab or a biosimilar version thereof, which formulation comprises from about 5% to about 20% of a therapeutic dose of bevacizumab or a biosimilar version thereof.

In another aspect, provided herein is a formulation comprising an anti-VEGF antibody provided herein, and at least one pharmaceutically acceptable excipient.

In general, the unit-dose formulations provided herein can be formulated for administration to a patient by any of the accepted modes of administration. Various formulations and drug delivery systems are available in the art. See, e.g., Remington's Pharmaceutical Sciences, edited by E. W. Martin (Mack Publishing Company, 18th ed., 1990).

In general, unit-dose formulations provided herein will be administered as pharmaceutical compositions by any one of the following routes: oral, systemic (e.g., transdermal, intranasal or by suppository), or parenteral (e.g., intramuscular, intravenous or subcutaneous) administration.

The unit-dose formulations may be comprised of in general, an anti-VEGF antibody, optionally in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 18th ed., 1990).

The present formulations may, if desired, be presented in a pack or dispenser device containing a unit-dose of the active ingredient. Such a pack or device may, for example, comprise metal or plastic foil, such as a blister pack, or glass, and rubber stoppers such as in vials. The pack or dispenser device may be accompanied by instructions for administration. Compositions comprising a unit-dose formulation of the invention formulated in a compatible pharmaceutical carrier may also be prepared, placed in an appropriate container, and labeled for treatment of an indicated condition.

Kits

In some aspects, the current invention relates to kits comprising: (a) an amount of an albumin-bound chemotherapeutic/anti-VEGF antibody complexes, (b) a unit dose of a sub-therapeutic amount of anti-VEGF antibody, and optionally (c) instructions for use.

In some embodiments, the kits can include lyophilized complexes of the albumin-bound chemotherapeutic/anti-VEGF antibody.

In some preferred embodiments, the kit components can be configure in such a way that the components are accessed in their order of use. For example, in some aspects the kit can be configured such that upon opening or being accessed by a user, the first component available is the unit dose of a sub-therapeutic amount of anti-VEGF antibody, for example, in a first vial. A second container (e.g., a vial) comprising or containing an amount of the albumin-bound chemotherapeutic/anti-VEGF antibody complexes can then be accessed. As such the kits can be intuitively configured in a way such that the first vial must be opened prior to the second vial being opened. It should be understood that in some embodiments, the order can be different, for example, where it is desired to administer the complex first, prior to the administration of the antibody. Also, it can be configured such that both are administered at the same time. Finally, it should be understood that additional vials or containers of either or both component(s) can be included, and configured for opening in any desired order. For example, the first vial could be antibody, the second vial could include complex, a third could include either antibody or complex, etc. It is contemplated that a kit configured in such a way would prevent, or at least help to prevent, the components from being administered in an order not intended by the instructions for use.

In some aspects, the invention is directed to a kit of parts for administration of albumin-bound chemotherapeutic/anti-VEGF antibody complexes and a unit dose of a sub-therapeutic amount of anti-VEGF antibody; and optionally further comprising a dosing treatment schedule in a readable medium. In some embodiments, the dosing schedule includes the sub-therapeutic amount of anti-VEGF antibody required to achieve a desired average serum level is provided. In some embodiments, the kit of parts includes a dosing schedule that provides an attending clinician the ability to select a dosing regimen of the sub-therapeutic amount of anti-VEGF antibody based on the sex of the patient, mass of the patient, and the serum level that the clinician desires to achieve. In some embodiments, the dosing treatment is based on the level of circulating VEGF in the blood of the patient. In some embodiments, the dosing schedule further provides information corresponding to the volume of blood in a patient based upon weight (or mass) and sex of the patient. In an embodiment, the storage medium can include an accompanying pamphlet or similar written information that accompanies the unit dose form in the kit. In an embodiment, the storage medium can include electronic, optical, or other data storage, such as a non-volatile memory, for example, to store a digitally-encoded machine-readable representation of such information.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

EXAMPLES

The present disclosure is illustrated using a pre-treatment of bevacizumab (i.e., AVASTIN®) followed by nanoparticles composed of albumin-bound paclitaxel (i.e., ABRAXANE®) and bevacizumab (i.e., AVASTIN®).

One skilled in the art would understand that making and using the nanoparticles, as well as administration of a co-treatment of bevacizumab, of the Examples are for the sole purpose of illustration, and that the present disclosure is not limited by this illustration.

Any abbreviation used herein, has normal scientific meaning. All temperatures are ° C. unless otherwise stated. Herein, the following terms have the following meanings unless otherwise defined:
ABX=ABRAXANE®/(albumin-bound
ADC=antibody dependent chemotherapy
BEV=bevacizumab
BSA=bovine serum albumin
$dH_2O$=distilled water
kg=kilogram
nM=nano molar
mg=milligram
ml or mL=milliliter
$m^2$=square meters
$mm^3$=cubic millimeter
μg microgram
μl=microliter
μm=micrometer/micron
PBS=Phosphate buffered saline Example 1: Nanoparticle Preparation ABRAXANE® (ABX) (10 mg) was suspended in bevacizumab (BEV) (4 mg [160 μl] unless otherwise indicated), and 840 μl of 0.9% saline was added to give a final concentration of 10 mg/ml and 2 mg/ml of ABX and BEV, respectively. The mixture was incubated for 30 minutes at room temperature (or at the temperature indicated) to allow particle formation. For Mastersizer experiments to measure particle size of ABX:BEV complexes, 10 mg of ABX was suspended in BEV at concentrations of 0 to 25 mg/ml. Complexes of ABX with rituximab (0-10 mg/ml) or trastuzumab (0-22 mg/ml) were formed under similar conditions.

For use in humans, the ABXBEV complexes may be prepared by obtaining the dose appropriate number of 4 mL vials of 25 mg/mL BEV and diluting each vial per the following directions to 4 mg/mL. The dose appropriate number of 100 mg vials of ABX can be prepared by reconstituting to a final concentration containing 10 mg/mL ABX nanoparticles. Using a sterile 3 mL syringe, 1.6 mL (40 mg) of bevacizumab (25 mg/mL) can be withdrawn and slowly injected, over a minimum of 1 minute, onto the inside wall of each of the vials containing 100 mg of ABX. The bevacizumab solution should not be injected directly onto the lyophilized cake as this will result in foaming. Then, using a sterile 12 mL sterile syringe, 8.4 mL 0.9% Sodium Chloride Injection, USP, can be withdrawn and slowly injected, over a minimum of 1 minute, 8.4 mL onto the inside wall of each vial containing ABX 100 mg and BEV 40 mg. Once the addition of BEV 1.6 mL and 0.9% Sodium Chloride Injection, USP 8.4 mL is completed, each vial can be gently swirled and/or inverted slowly for at least 2 minutes until complete dissolution of any cake/powder occurs. Generation of foam should be avoided. At this point, the concentration of each vial should be 100 mg/10 mL ABX and 40 mg/10 mL BEV. The vials containing the ABX and BEV should sit for 60 minutes. The vial(s) should be gently swirled and/or inverted every 10 minutes to continue to mix the complex. After 60 minutes has elapsed, the calculated dosing volume of ABX and BEV should be withdrawn from each vial and slowly added to an empty viaflex bag. An equal volume of 0.9% Sodium Chloride Injection, USP is then added to make the final concentration of ABX 5 mg/mL and BEV 2 mg/mL. The bag should then be gently swirled and/or inverted slowly for 1 minute to mix. The ABX:BEV nanoparticles can be stored for up to 4 hours at room temperature following final dilution.

Example 2: Co-Treatment with BEV Improves Targeting of ABX/BEV Complexes

Athymic nude mice were injected with 1×106 A375 human melanoma cells in the right flank and then treated with PBS, 12 mg/kg BEV, 30 mg/kg ABX AB160, or pretreated with 1.2 mg/kg BEV and, 24 hr later, AB160. AB160 was prepared as described in PCT Application No. PCT/US15/54295 and Example 1 above. FIGS. 1A-E track tumor size over 40 days (all mice in the PBS, BEV, and ABX died by day 20). Data is represented as tumor volume in mm$^3$. Only mice treated with AB160 (with or without pretreatment with BEV) showed a reduction in average tumor volume. See also FIG. 1F and FIG. 1G.

Figure 1F:
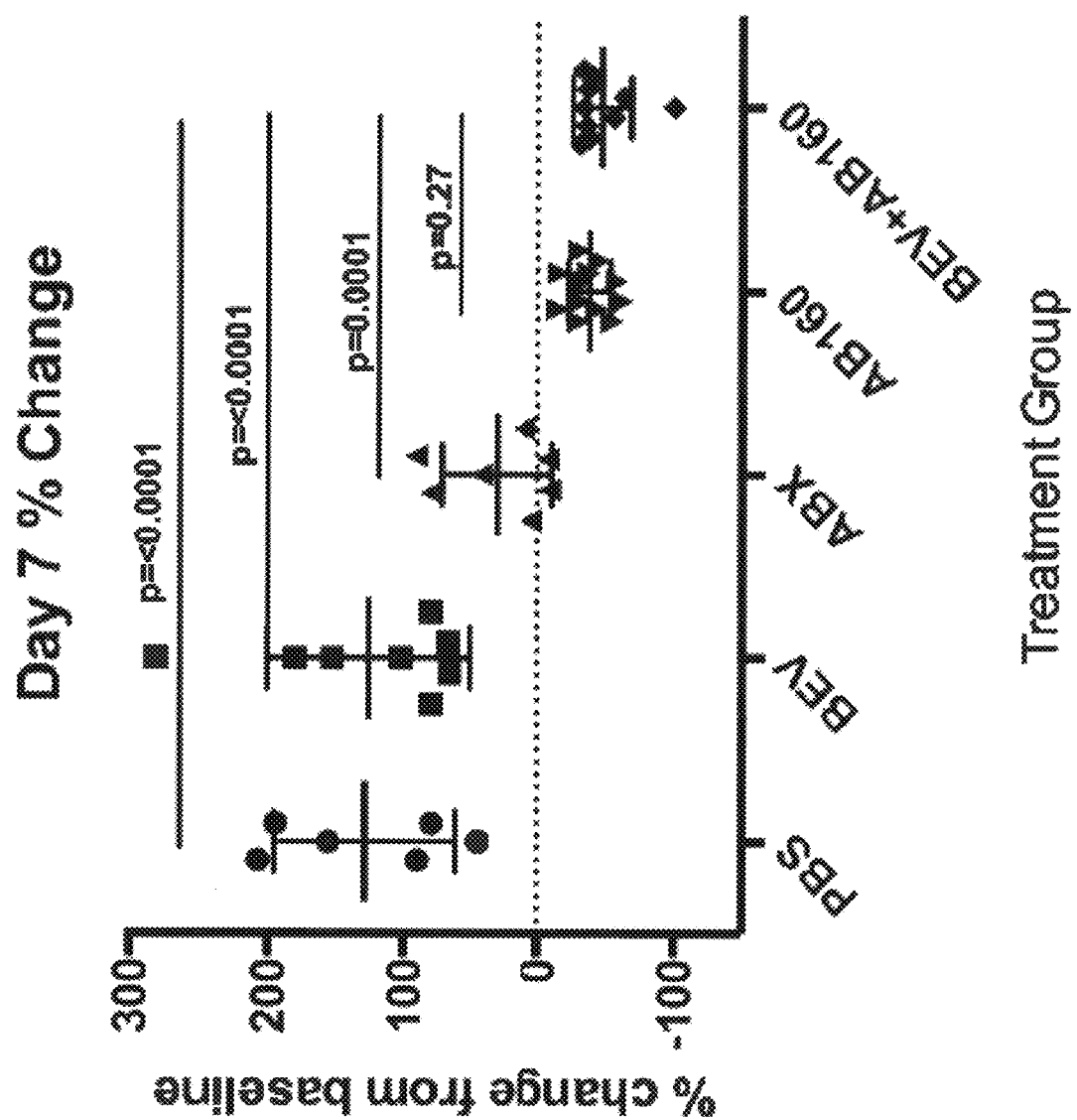
FIG. 1F summarizes the day 7-post treatment data from FIGS. 1A-E.
Figure 1G:
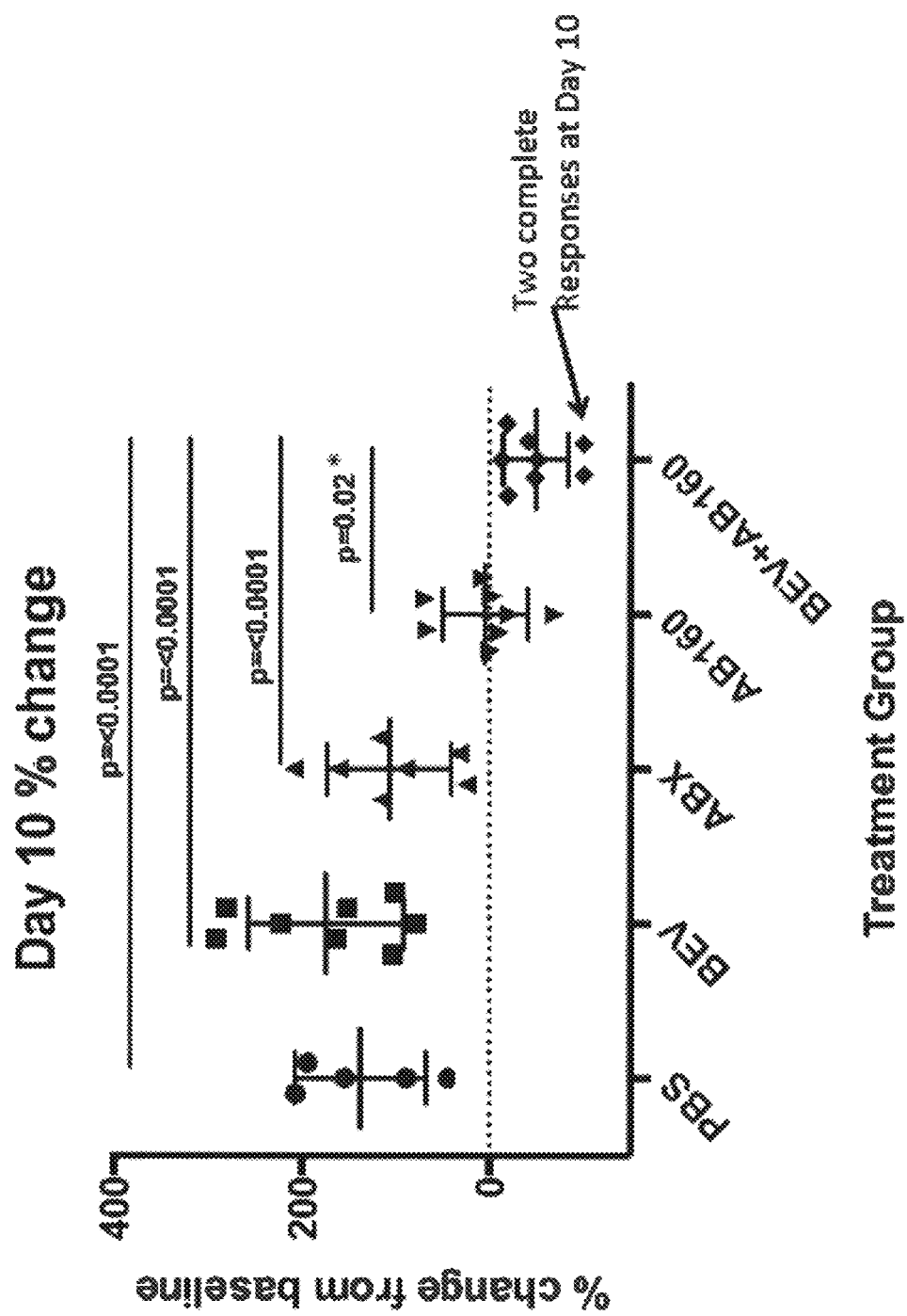
FIG. 1G summarizes the day 10-post treatment data from FIGS. 1A-E.

The day 7-post treatment data, as summarized in FIG. 1F, show that pretreatment with BEV was associated with a statistically significant reduction in tumor volume over control or BEV alone ($p \leq 0.0001$), or ABX alone ($p \leq 0.0001$).

The day 10-post treatment data, as summarized in FIG. 1G, again show that pretreatment with BEV was associated with a statistically significant reduction in tumor volume over control or BEV alone ($p \leq 0.0001$), or ABX alone ($p \leq 0.0001$). Pretreatment with BEV before AB160 was also associated with a reduction in tumor volume over AB160 alone ($p = 0.02$), with complete response in two mice.

In this experiment, a 12 mg/kg dose of BEV was not therapeutic. The amount of BEV added in the pretreatment group was only 1.2 mg/kg, which is 1/10 the usual dose in mice. Yet pretreatment with a subtherapeutic dose improved the efficacy of the AB160 nanoparticles. This data support the idea that pretreatment with a subtherapeutic amount of BEV can clear systemic levels of VEGF, leaving a greater relative concentration at the tumor such that tumor-associated VEGF targeting by the AB160 nanoparticles is more effective.

Figure 2:
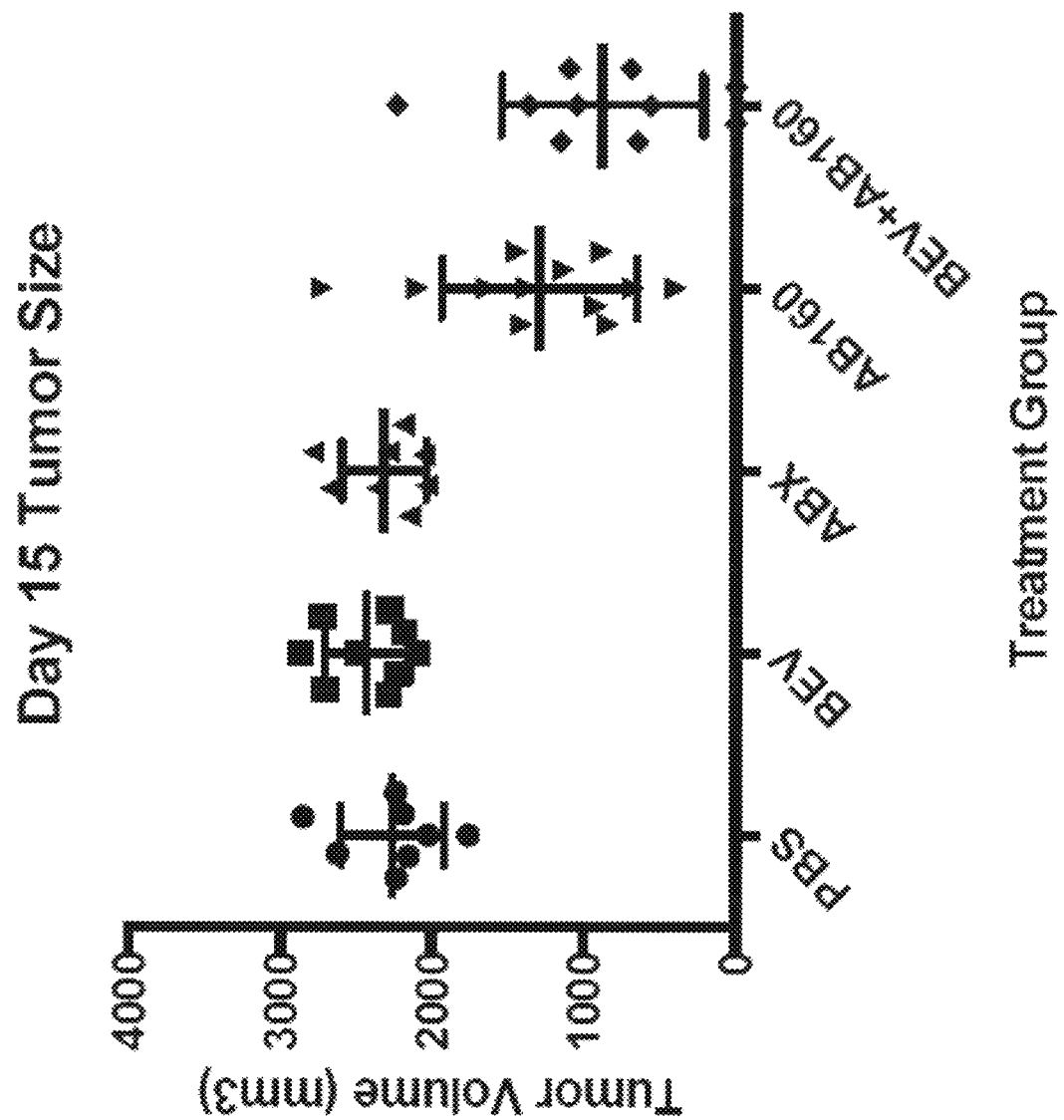
FIG. 2 depicts the tumor measurements on day 15-post treatment with either saline (PBS), bevacizumab (BEV), ABRAXANE® (ABX), AB160 or co-treatment with BEV one day (24 hours) prior to administration of AB160 (BEV+AB160).
Figure 3:
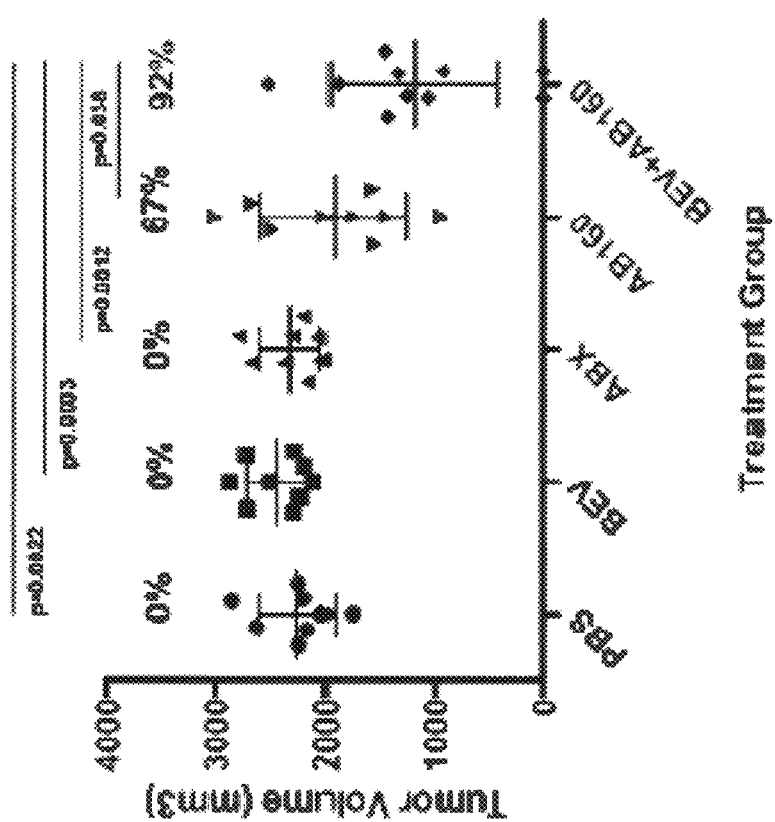
FIG. 3 depicts the tumor measurements on day 20-post treatment with either saline (PBS), bevacizumab (BEV), ABRAXANE® (ABX), AB160 or co-treatment with BEV one day (24 hours) prior to administration of AB160 (BEV+AB160).

Tumors were measured on day 15 following treatment with either saline (PBS), AVASTIN® (BEV), ABRAXANE® (ABX), AB160 or a pretreatment of BEV one day before AB160 (BEV+AB160). A 10% sub-therapeutic dose of BEV, as compared to the dose give to the BEV alone or AB160 cohort, was given to the BEV+AB160 cohort 24 hours prior to administration of the AB160. The BEV+AB160 cohort presented with delayed tumor growth, even when compared to AB160, with two mice presenting with complete cures. FIG. 2. As summarized in Table 1, these experiments also show that pre-treatment with BEV+AB160, increases survival. At day 15, 100% of the mice in the BEV+AB160 cohort were alive, whereas 86% of these mice in the AB160 cohort were still alive. Both treatment groups had substantially greater survival than the PBS, BEV-only, or ABX-only treatment groups which exhibited a 0%, 0% and 11% survival rate, respectively. At day 20, 92% of the mice in the BEV+AB160 cohort were alive, whereas 67% of the mice in the AB160 cohort were still alive. FIG. 3.

TABLE 1

| Percentage of mice alive on day 15 | | | | | |
|---|---|---|---|---|---|
| Treatment Group | PBS | BEV | ABX | AB160 | BEV + AB160 |
| Percent Alive on day 15 | 0% | 0% | 11% | 86% | 100% |

Figure 4:
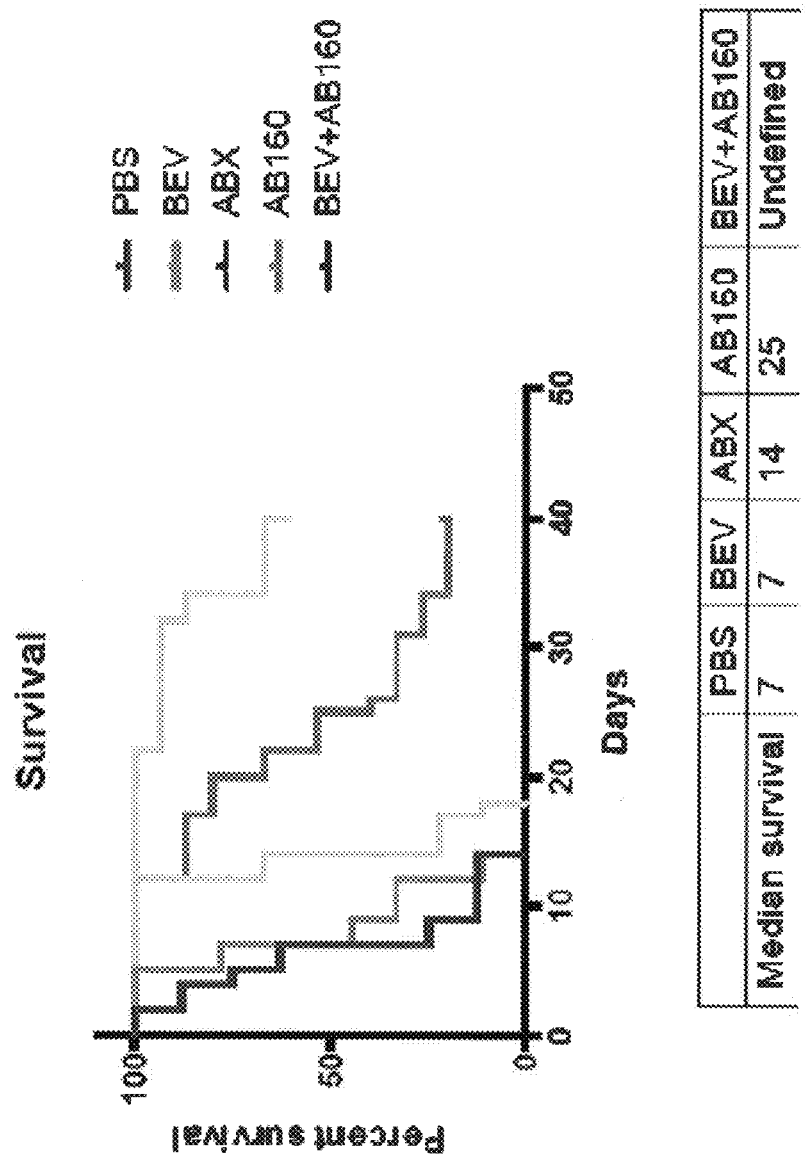
FIG. 4 depicts the median survival with either saline (PBS), bevacizumab (BEV), ABRAXANE® (ABX), AB160 or co-treatment with BEV one day (24 hours) prior to administration of AB160 (BEV+AB160).

Survival was again assessed at day 40. FIG. 4. As shown median survival of both the mice treated with PBS or BEV was 7 days. Mice treated with ABX alone shown median survival of 14 days, while those treated with AB160 exhibited a median survival of 25 days.

Median survival of mice co-treated with BEV and AB160 remained undefined, with approximately 50% of the mice co-treated with BEV and AB160 still alive, at day 40.

Example 3 Fluorescence Over Time of AlexaFluor 750 Labeled Nanoparticles

Figure 5:
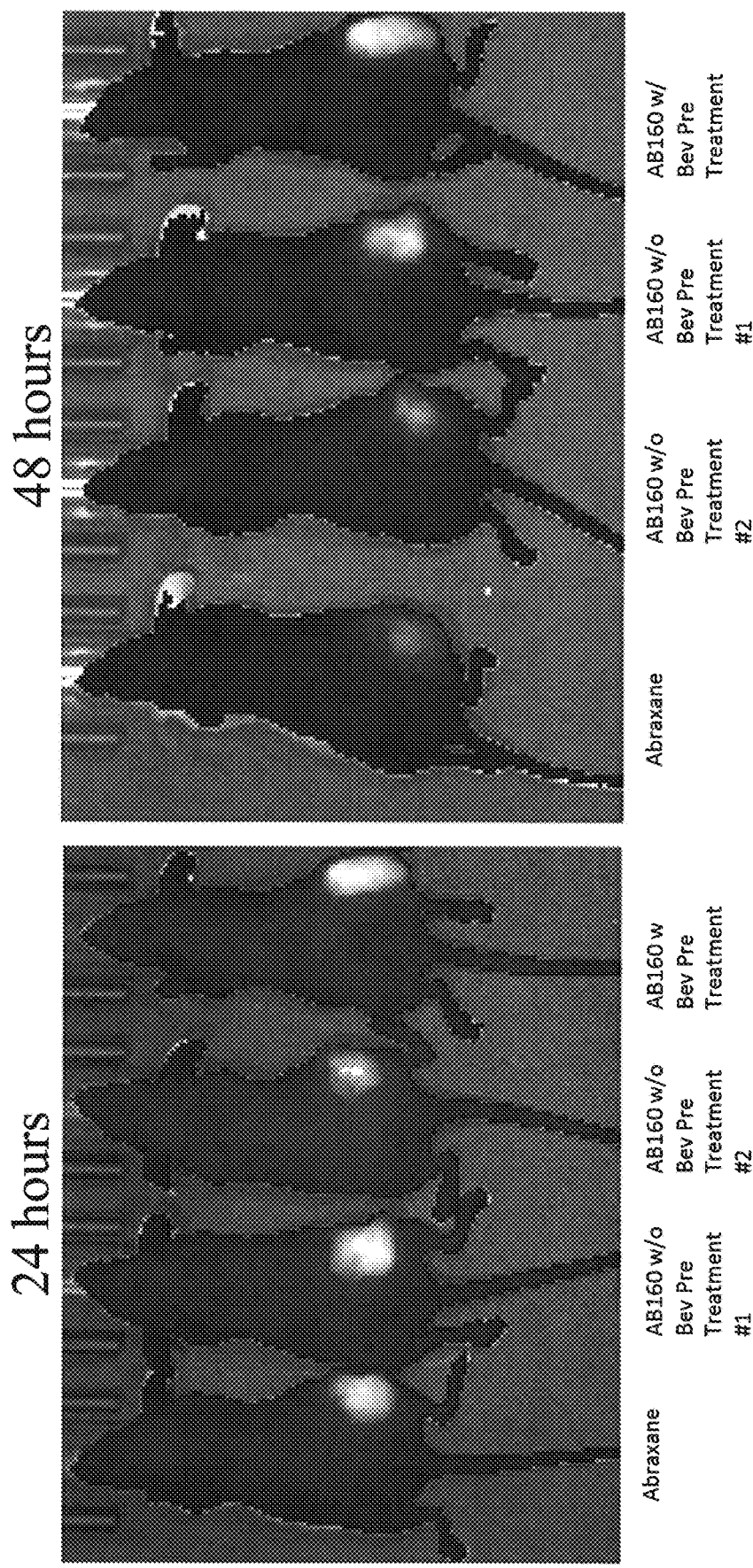
FIG. 5 is fluorescent imagery of mice treated with AB160 with or without a bevacizumab (BEV) pre-treatment. The fluorescent imagery was performed at an excitation/emission spectrum of 710/760.

Mice received IV injections of equal amounts of either labeled ABRAXANE®, or nanoparticles of ABRAXANE® having surface complexation with bevacizumab (BEV) as per Example 1 above (AB160); one AB160 group of mice received a pre-treatment 1.2 mg/kg of bevacizumab. Fluorescent imagery was done at an excitation/emission spectrum of 710/760 (FIG. 5). Regions of interest (ROI) in the mice of FIG. 5 were assigned by software to track tumor accumulation based on a fluorescence threshold. Fluorescence per unit area of background ROIs and tumor ROIs for all three treatment groups were determined at 24, 29, and 48 hours post injection The amount of fluorescence (and thus paclitaxel) in the tumor and background ROIs at 24, 29 and 48 hour presented in FIGS. 7A and 7B. The data demonstrates that pretreatment with BEV results in higher levels of tumor fluorescence as compared AB160 alone or ABRAXANE alone. Furthermore, the clearance rate for AB160-treated mice with or without a BEV pre-treatment is nearly twice as slow as the ABRAXANE treated mice (FIG. 7C). These results evidence that pretreatment with BEV and use of ABRAXANE® nanoparticles having surface complexation with BEV provides for a method for increasing the duration of tumor uptake of albumin containing a chemotherapeutic agent both at 24 hours and 48 hours. Likewise, use of ABRAXANE® nanoparticles having surface complexation with BEV also provides for increasing the duration of tumor uptake of these albumin containing nanoparticles with or without pretreatment with BEV at 48 hours. Both of these results evidence continued uptake for 48 hours and possibly out to 72 hours. On the other hand, background fluorescence of the corresponding nanoparticles is projected to go to about 0 at 72 hours evidencing that systemic circulation of the drugs have disappeared from all parts of the animal but for the tumor. All told, the incorporation of the BEV into ABRAXANE® has a stabilizing impact, which is most evident by the concentration of the drug in the tumor at 48 hours and projected for 72 hours. Without being limited to any theory, the antibody coating of the albumin nanoparticles imparts stability possibly by reducing liver or kidney clearance and/or by reducing protease degradation of the albumin carrier. This approach allows targeting antibodies to complex with a protein carrier such as albumin and any chemotherapeutic drug, such as, e.g., abiraterone, bendamustine, bortezomib, carboplatin, cabazitaxel, cisplatin, chlorambucil, dasatinib, docetaxel, doxorubicin, epirubicin, erlotinib, etoposide, everolimus, 5-fluoruracil, gefitinib, idarubicin, imatinib, hydroxyurea, imatinib, lapatinib, leuprorelin, melphalan, methotrexate, mitoxantrone, nedaplatin, nilotinib, oxaliplatin, paclitaxel, pazopanib, pemetrexed, picoplatin, romidepsin, satraplatin, sorafenib, vemurafenib, sunitinib, teniposide, triplatin, vinblastine, vinorelbine, vincristine, and cyclophosphamide thereby providing prolonged delivery of such drugs to the tumor.

Figure 7A:
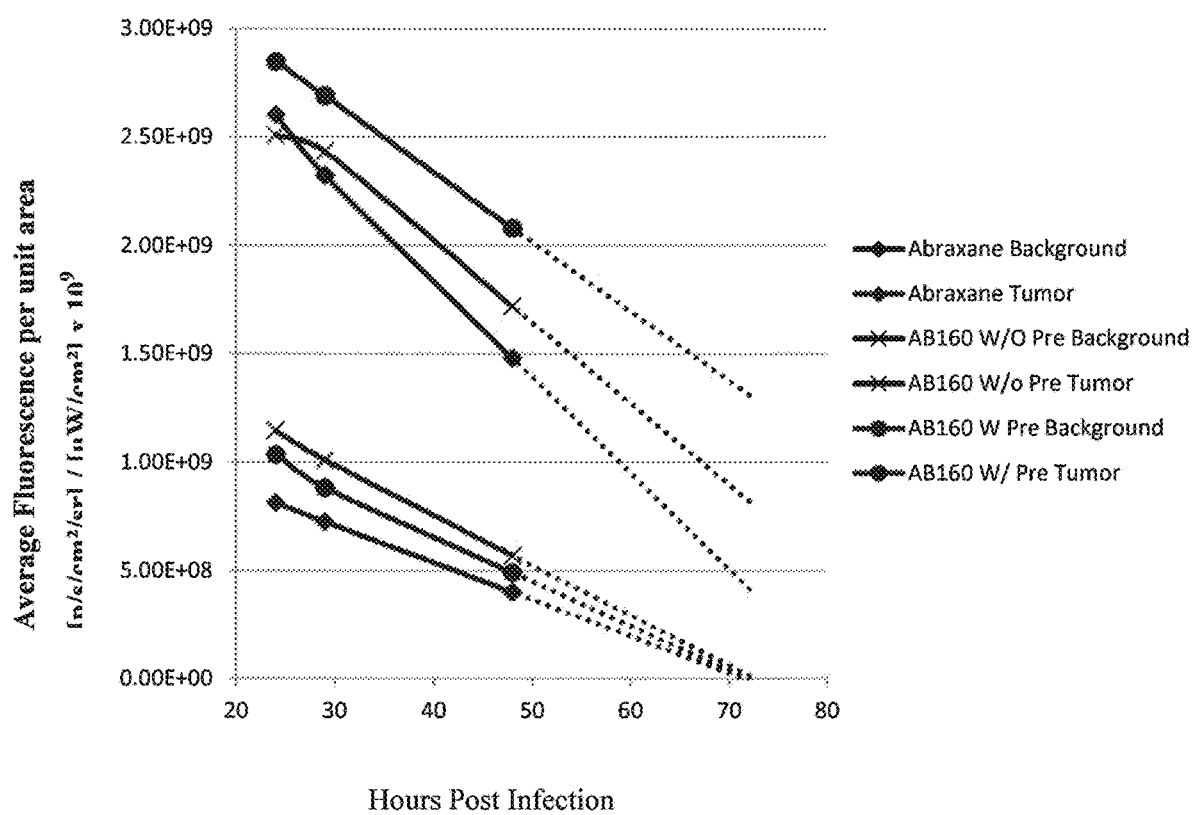
FIG. 7A depicts fluorescence per unit area of tumor ROI's (upper three lines) and background ROIs (lower three lines) for all three treatment groups at 24, 29 and 48 hours post injection. The dotted line represents an extrapolation of fluorescence, indicating an expected complete clearance at about 72 hours.
Figures 7B, 7C:
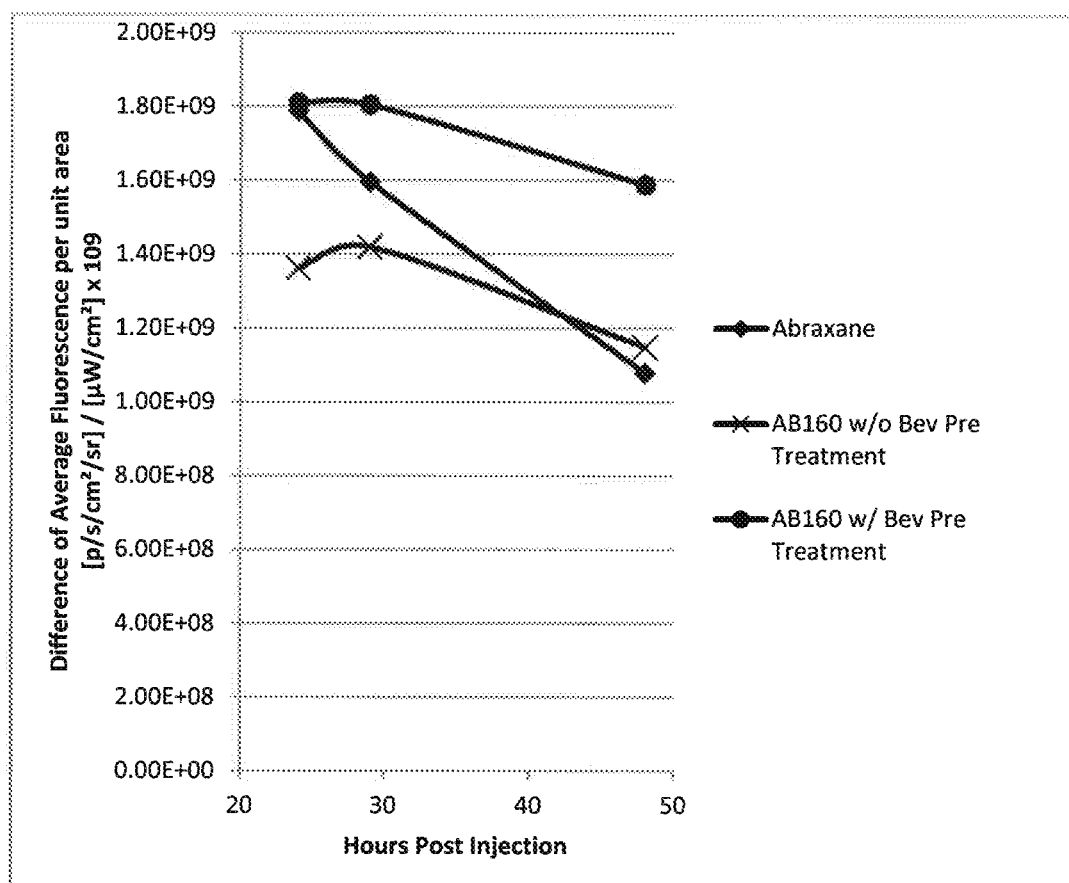
FIG. 7B depicts the clearance from tumor ROIs adjusted for background fluorescence.
FIG. 7C is a table of the clearance rates of fluorescent nanoparticles indicating AB160 nanoparticles are cleared nearly twice as slowly as ABRAXANE®.

FIG. 7A indicates that at 24 hours the total amount of fluorescence accumulating in the tumor of AB160-treated mice without a BEV pretreatment was less than that achieved in ABRAXANE®-treated mice. However, the rate of clearance of ABRAXANE® in treated mice was higher than AB160 in treated mice. Therefore if one were to extrapolate the data in FIG. 7A, as shown by the dotted line, the level of fluorescence (and thus paclitaxel) would be maintained at a higher level in the tumors of AB160-treated mice with or without BEV pre-treatment than the level maintained by ABRAXANE treatment.

FIG. 7 also demonstrates that the background fluorescence in AB160-treated mice with or without pretreatment is higher than that in ABRAXANE-treated mice. While not wishing to be bound by theory, this suggests that the antibodies confer additional stability to the nanoparticles of paclitaxel and albumin such that they are cleared more slowly from the circulation than ABRAXANE alone. This would be advantageous as it would provide higher levels of the nanoparticles for longer periods of time for subsequent infiltration into the tumor.

Example 16: Nanoparticles Having a Size of 225 nm

Figure 6:
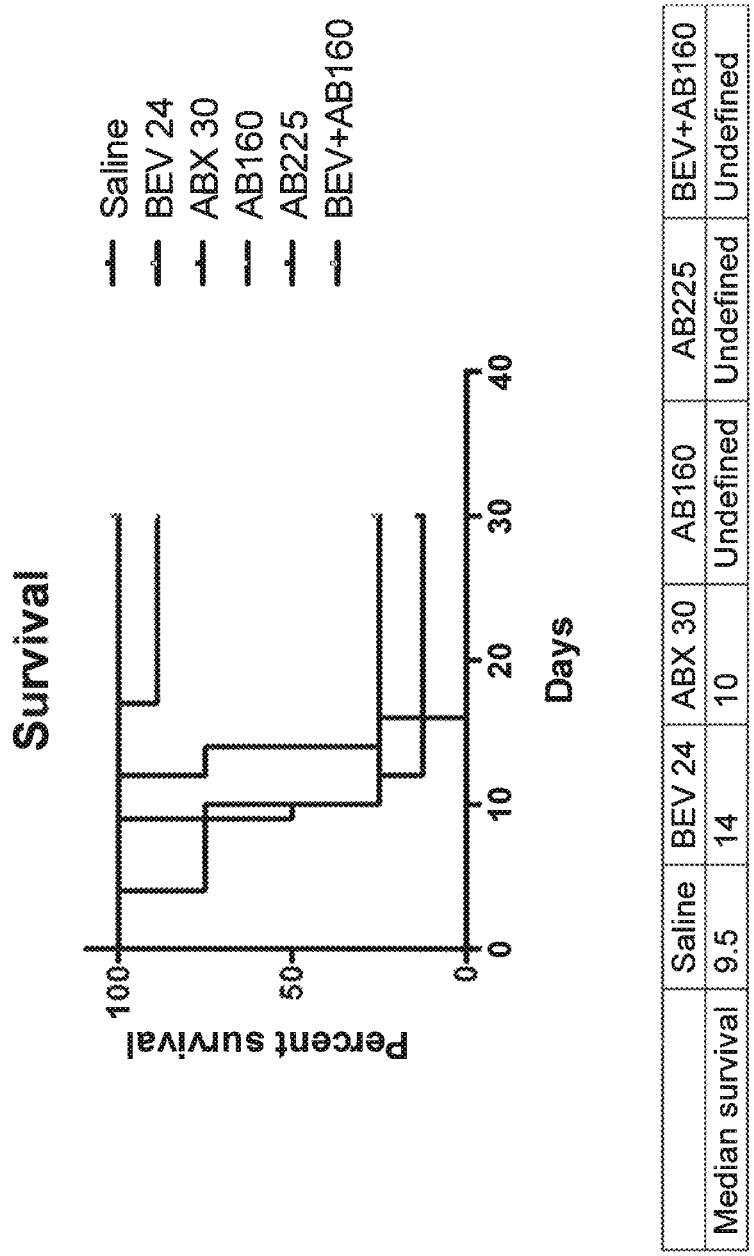
FIG. 6, depicts the median survival with either saline (PBS), bevacizumab (BEV), ABRAXANE® (ABX), AB160 alone, AB225 and co-treatment with BEV prior to administration of AB160 (BEV+AB160).

To make a nanoparticle having a size of 225 nm, the particles were prepared in accordance with Example 1 but the ratio of BEV to ABRAXANE® was 4:5, i.e., 4 parts BEV and 5 parts ABRAXANE. This ratio produced nanoparticles having a size of 225 nm (AB225). The effect of AB225 was assayed in animals as set forth above. FIG. 6 demonstrates that the survival of the mice treated with a single dose of saline, BEV24 (24 mg/kg), ABX30(30 mg/kg), AB160 (12 mg/kg BEV and 30 mg/kg ABX) and AB225 (24 mg/kg BEV and 30 mg/kg ABX) and with AB160 with a BEV (1.2 mg/kg) pretreatment. At 30 days the survival of mice treated with AB225, and with AB160 with or without pretreatment with BEV far exceeded the survival of mice treated with BEV alone of ABRAXANE® alone.

What is claimed is:

1. A method for treating a patient suffering from a cancer which expresses VEGF wherein said patient is treated with a sub-therapeutic amount of an anti-VEGF antibody and albumin-bound chemotherapeutic/anti-VEGF antibody nanoparticle complexes containing a therapeutically effective amount of the chemotherapeutic such that the administration of said sub-therapeutic amount of the anti-VEGF antibody enhances the efficacy of said nanoparticle complexes, wherein the sub-therapeutic amount of anti-VEGF antibody is administered from between about 30 minutes to about 48 hours prior to administration of the albumin-bound chemotherapeutic/anti-VEGF antibody nanoparticle complexes; wherein the chemotherapeutic is paclitaxel and the anti-VEGF antibody is bevacizumab or a biosimilar version thereof, wherein a therapeutic dosage of the anti-VEGF antibody is about 5 mg/kg to about 15 mg/kg; and wherein the sub-therapeutic amount of anti-VEGF antibody is selected from an amount consisting of about 1%, about 5%, about 10%, about 15%, about 20%, about 25%, about 30%, about 35%, about 40%, about 45%, about 50%, about 55%, and about 60% of the therapeutic dosage of anti-VEGF antibody.

2. The method of claim 1, wherein the sub-therapeutic amount of anti-VEGF antibody is an amount which blocks circulating VEGF without blocking VEGF on a target of said nanoparticle complexes.

3. The method of claim 2, wherein the target of said nanoparticle complexes is a solid cancer.

4. The method of claim 1, wherein the sub-therapeutic amount of anti-VEGF antibody to be administered to the patient is determined by analyzing the level of circulating VEGF in the blood.

5. A method for enhancing the efficacy of albumin-bound chemotherapeutic/anti-VEGF antibody nanoparticle complexes by administering the albumin-bound chemotherapeutic/anti-VEGF antibody nanoparticle complexes about 24 hours after administrating a sub-therapeutic amount of anti-VEGF antibody to a patient in need thereof; wherein the chemotherapeutic is paclitaxel and the anti-VEGF antibody is bevacizumab or a biosimilar version thereof, wherein a therapeutic dosage of the anti-VEGF antibody is about 5 mg/kg to about 15 mg/kg; and wherein the sub-therapeutic amount of anti-VEGF antibody is selected from an amount consisting of about 1%, about 5%, about 10%, about 15%, about 20%, about 25%, about 30%, about 35%, about 40%, about 45%, about 50%, about 55%, and about 60% of the therapeutic dosage of anti-VEGF antibody.

6. The method of claim 5, wherein the sub-therapeutic amount of anti-VEGF antibody is an amount which blocks circulating VEGF without blocking VEGF on a target of said nanoparticle complexes.

7. The method of claim 6, wherein the target of said nanoparticle complexes is a solid cancer.

8. The method of claim 5, wherein the sub-therapeutic dose of anti-VEGF antibody to be administered to the patient is determined by analyzing the level of circulating VEGF in the blood.

9. The method of claim 5, wherein the sub-therapeutic dose of the anti-VEGF antibody is administered from between about 30 minutes to about 48 hours prior to administration of the albumin-bound chemotherapeutic/anti-VEGF antibody nanoparticle complexes.

10. A method for enhancing the therapeutic outcome in a patient suffering from a cancer expressing soluble VEGF which patient is being treated with nanoparticle complexes comprising albumin-bound chemotherapeutic and anti-VEGF antibodies wherein said antibodies of the nanoparticle complexes are integrated onto and/or into said nanoparticle complexes, which method comprises treating said patient with a sub-therapeutic amount of said anti-VEGF antibody prior to treatment with the nanoparticle complexes; wherein the chemotherapeutic is paclitaxel and the anti-VEGF antibody is bevacizumab or a biosimilar version thereof, wherein a therapeutic dosage of the anti-VEGF antibody is about 5 mg/kg to about 15 mg/kg; and wherein the sub-therapeutic amount of anti-VEGF antibody is selected from an amount consisting of about 1%, about 5%, about 10%, about 15%, about 20%, about 25%, about 30%, about 35%, about 40%, about 45%, about 50%, about 55%, and about 60% of the therapeutic dosage of anti-VEGF antibody.

11. A method for enhancing the therapeutic outcome in a patient suffering from a cancer overexpressing soluble VEGF which patient has been treated with a sub-therapeutic amount of anti-VEGF antibody, said method comprising treating said patients with an effective amount of nanoparticle complexes comprising albumin-bound paclitaxel and anti-VEGF antibodies wherein said antibodies of the nanoparticle complexes are integrated onto and/or into said nanoparticle complexes; wherein the anti-VEGF antibody is bevacizumab or a biosimilar version thereof, wherein a therapeutic dosage of the anti-VEGF antibody is about 5 mg/kg to about 15 mg/kg; and wherein the sub-therapeutic amount of anti-VEGF antibody is selected from an amount consisting of about 1%, about 5%, about 10% about 15%, about 20%, about 25%, about 30%, about 35%, about 40%, about 45%, about 50%, about 55%, and about 60% of the therapeutic dosage of anti-VEGF antibody.

* * * * *

UNITED STATES PATENT AND TRADEMARK OFFICE
CERTIFICATE OF CORRECTION

| | | |
|---|---|---|
| PATENT NO. | : 10,561,726 B2 | Page 1 of 1 |
| APPLICATION NO. | : 15/092403 | |
| DATED | : February 18, 2020 | |
| INVENTOR(S) | : Swiss et al. | |

It is certified that error appears in the above-identified patent and that said Letters Patent is hereby corrected as shown below:

On the Title Page

Item (56) References Cited, OTHER PUBLICATIONS, Page 9, Column 1, Line 47:
Please correct "Feb. 15, 2016." to read -- Dec. 15, 2016. --

Item (56) References Cited, OTHER PUBLICATIONS, Page 9, Column 1, Line 48:
Please correct "May 2, 2011." to read -- May 2, 2016. --

Item (56) References Cited, OTHER PUBLICATIONS, Page 9, Column 1, Line 61:
Please correct "May 31, 2017." to read -- May 31, 2018. --

Item (56) References Cited, OTHER PUBLICATIONS, Page 9, Column 2, Line 8:
Please correct "Hapa" to read -- Hara --

Item (56) References Cited, OTHER PUBLICATIONS, Page 9, Column 2, Line 73:
Please correct "Oct. 4, 2016." to read -- Oct. 4, 2018. --

Item (56) References Cited, OTHER PUBLICATIONS, Page 10, Column 2, Line 4:
Please correct "15/458,395" to read -- 15/456,395 --

Item (56) References Cited, OTHER PUBLICATIONS, Page 10, Column 2, Line 5:
Please correct "May 14, 2019," to read -- Aug. 14, 2019. --

Item (56) References Cited, OTHER PUBLICATIONS, Page 10, Column 2, Line 15:
Please correct "Lympnomas" to read -- Lymphomas --

Signed and Sealed this
Twenty-eighth Day of July, 2020

Andrei Iancu
*Director of the United States Patent and Trademark Office*